US007449309B2

(12) United States Patent
Longley

(10) Patent No.: US 7,449,309 B2
(45) Date of Patent: Nov. 11, 2008

(54) METHODS FOR DESENSITIZING A SUBJECT TO AN AGENT

(75) Inventor: B. Jack Longley, Hamden, CT (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 11/314,421

(22) Filed: Dec. 20, 2005

(65) Prior Publication Data

US 2006/0216282 A1 Sep. 28, 2006

Related U.S. Application Data

(63) Continuation of application No. 09/980,572, filed as application No. PCT/US00/12405 on May 5, 2000, now Pat. No. 6,977,159, which is a continuation-in-part of application No. 09/474,478, filed on Dec. 29, 1999, now Pat. No. 6,989,248, which is a continuation-in-part of application No. 09/306,143, filed on May 6, 1999, now Pat. No. 6,576,812.

(51) Int. Cl.
*C12N 15/09* (2006.01)
(52) U.S. Cl. .................................. 435/69.2; 530/389.2
(58) Field of Classification Search .................. 435/69.2
See application file for complete search history.

(56) References Cited

U.S. PATENT DOCUMENTS

| | | | |
|---|---|---|---|
| 5,877,396 A | 3/1999 | Ravetch et al. | |
| 5,911,988 A | 6/1999 | Brownell et al. | |
| 5,997,865 A | 12/1999 | Bennett et al. | |
| 6,576,812 B1 * | 6/2003 | Longley | 800/3 |
| 6,977,159 B1 * | 12/2005 | Longley | 435/69.2 |
| 6,989,248 B2 * | 1/2006 | Longley | 435/69.2 |
| 2003/0077282 A1 * | 4/2003 | Bigler et al. | 424/144.1 |

OTHER PUBLICATIONS

Anderson, D.M., et al. (1990) "Molecular Cloning of Mast Cell Growth Factor, a Hematopoietin That Is Active in Both Membrane Bound and Soluble Forms," Cell 63:235-243.
Bradl, M., et al., (1991) "Clonal coat color variation due to a transforming gene expressed in melanocytes of transgenic mice," Proc. Nat. Acad. Sci. USA 88:6447-6451.
Costa, J.J., et al. (1996) "Recombinant Human Stem Cell Factor (Kit Ligand) Promotes Human Mast Cell and Melanocyte Hyperplasia and Functional Activation in Vivo,", J. Exp. Med. 183:2681-2686.
Funasaka, Y., et al. (1992) "c-Kit-Kinase Induces a Cascade of Protein Tyrosine Phosphorylation in Normal Human Melanocytes in Response to Mast Cell Growth Factor and Stimulates Mitogen-Activated Protein Kinase But is Down-Regulated in Melanomas," Mol. Biol. Cell 3:197-209.
Furitsu, T., et al. (1993) "Identification of Mutations in the Coding Sequence of the Protooncogene *c-kit* in a Human Mast Cell Leukemia Cell Line Causing Ligand-Independent Activation of *c-kit* Product," J. Clin. Invest. 92:1736-1744.

Grichnik, J.M., et al., (1995) "Human recombinant stem-cell factor induces melanocytic hyperplasia in susceptible patients," J. Am. Acad. Dermol. 33:577-583.
Hamann, K., et al., (1995) "Expression of stem cell factor in cutaneous mastocytosis," Br. J. Dermatol. 133:203-208.
Harrist, T.J., et al. (1995) "Recombinant human stem cell factor(SCF) (c-kit ligand) promotes melanocyte hyperplasia and activation in vivo," Lab. Invest. 72:48A.
Hirobe, T. (1984) "Histochemical Survey of the Distribution of the Epidermal Melanoblasts and Melanocytes in the Mouse During Fetal and Postnatal Periods," Anat. Rec. 208:589-594.
Longley, J., et al., (1995) "The mast cell and mast cell disease," J. Am. Acad. Dermatol. 32:545-561.
Longley, B.J., Jr., et al. (1993) "Altered Metabolism of Mast-Cell Growth Factor (*c-kit* Ligand) in Cutaneous Mastocytosis," N. Engl. J. Med. 328:1302-1307.
Longley, B.J., et al. (1996) "Somatic *c-kit* activating mutation in urticaria pigmentosa and aggressive mastocytosis: establisHment of clonality in a human mast cell neoplasm," Nat. Genet. 12:312-314.
Lu, H.S., et al. (1991) "Amino Acid Sequence and Post-translation Modification of Stem Cell Factor Isolated from Buffalo Rat Liver Cell-conditioned Medium," J. Biol. Chem. 266:8102-8107.
Nishikawa, S., et al. (1991) "*In utero* manipulation of coat color formation by a monoclonal anti-*c-kit* antibody: two distinct waves of *c-kit* -dependency during melanocyte development," EMBO J. 10:2111-2118.
Okura, M., et al. (1995) "Effects of Monoclonal Anti-c-Kit Antibody (ACK2) on Melanoctes in Newborn Mice," J. Invest. Dermatol. 105:322-328.
Weiss, R.R., et al. (1995) "Human Dermal Endothelial Cells Express Membrane-Associated Mast Cell Growth Factor," J. Invest. Dermatol. 104:101-106.
Tsai, M., et al. (1991) "The Rat *c-kit* Ligand, Stem Cell Factor, Induces the Development of Connective Tissue-type and Mucosal Mast Cells in Vivo. Analysis by Anatomical Distribution, Histochemistry, and Protease Phenotype," J. Exp. Med. 174:125-131.
Vassar, R., et al. (1989) "Tissue-specific and differentiation-specific expression of a human K14 keratin gene in transgenic mice," Proc. Natl. Acad. Sci. USA 86:1563-1567.
Williams, D.E., et al. (1990) "Identification of a Ligand for the *c-kit* Proto-Oncogene," Cell 63:167-174.
Yarden, Y., et al. (1987) "Human proto-oncogene *c-kit*: a new cell surface receptor tyrosine kinase for an unidentified ligand," EMBO J. 6:3341-3351.
Yoshida, H., et al. (1996) "Distinct stages of melanocyte differentiation revealed by analysis of nonuniform pigmentation patterns," Development 122:1207-1214.

(Continued)

*Primary Examiner*—Ralph Gitomer
(74) *Attorney, Agent, or Firm*—John P. White; Cooper & Dunham LLP

(57) ABSTRACT

This invention provides a method of preventing or treating in a subject contact dermatitis which comprises administering to the subject an amount of a compound capable of inhibiting the stem cell factor signaling pathway effective to prevent or treat contact dermatitis so as to thereby prevent or treat contact dermatitis in the subject. This invention also provides a method of preventing or treating in a subject hyperpigmentation, asthma, cutaneous inflammation, anaphylaxis and bronchospasm, mastocytosis, tumors which express activated kit, and conception.

1 Claim, 13 Drawing Sheets

OTHER PUBLICATIONS

Yoshida, H., et al. (1996) "Neural and Skin Cell-Specific Expression Pattern Conferred by Steel Factor Regulatory Sequence in Transgenic Mice," Dev. Dyn. 207:222-232.

Zsebo, K.M., et al. (1990) "Stem Cell Factor Is Encoded at the Sl Locus of the Mouse and Is the Ligand for the *c-kit* Tyrosine Kinase Receptor," Cell 63:213-224.

Houdebine, L.M. (1994) "Production of pharmaceutical proteins from transgenic animals," J. Biotechnol. 34:269-287.

Kappel, C.A., et al. (1992) "Regulating gene expression in transgenic animals," Curr. Opin. Biotechnol. 3:548-553.

Sigmund, C.D. (2000) "Viewpoint: Are Studies in Genetically Altered Mice Out of Control?" Arterioscler. Thromb. Vasc. Biol. 20:1425-1429.

Wall, R.J. (1996) "Transgenic Livestock: Progress and Prospects for the Future," Theriogenology 45:57-68.

Amendment submitted Jan. 16, 2001 in connection with U.S. Appl. No. 09/306,143, filed May 6, 1999.

Amendment submitted Jan. 24, 2002 in connection with U.S. Appl. No. 09/306,143, filed May 6, 1999.

Amendment submitted Jun. 24, 2002 in connection with U.S. Appl. No. 09/306,143, filed May 6, 1999.

Communication submitted May 11, 2001 in connection with U.S. Appl. No. 09/306,143, filed May 6, 1999.

Communication submitted Nov. 4, 2002 in connection with U.S. Appl. No. 09/306,143, filed May 6, 1999.

Communication issued Apr. 23, 2002, including Notice to Comply in connection with U.S. Appl. No. 09/306,143, filed May 6, 1999.

Communication issued Oct. 2, 2002, including Notice to Comply in connection with U.S. Appl. No. 09/306,143, filed May 6, 1999.

Facsimile dated Dec. 13, 2002 in connection with U.S. Appl. No. 09/306,143, filed May 6, 2003.

Notice of Allowance issued Dec. 20, 2002, including Examiner's Amendment in connection with U.S. Appl. No. 09/306,143, filed May 6, 1999.

Office Action issued Apr. 11, 2001 in connection with U.S. Appl. No. 09/306,143, filed May 6, 1999.

Office Action issued Aug. 2, 2001 in connection with U.S. Appl. No. 09/306,143, filed May 6, 1999.

Office Action issued Jul. 13, 2000 in connection with U.S. Appl. No. 09/306,143, filed May 6, 1999.

Office Action issued Mar. 31, 2005 in connection with U.S. Appl. No. 09/980,572, filed Sep. 23, 2002.

Preliminary Amendment And Information Disclosure Statement submitted Oct. 8, 1999 in connection with U.S. Appl. No. 09/306,143, filed May 6, 1999.

Ando A., et al. (1993) "Effects on chronic treatment with the *c-kit* ligand, stem cell factor on immunoglobulin E-dependant anaphylacis, genetically mast cell-deficient $Sl/Sl^d$ mice acquire anaphylactic responsiveness, but the congenic normal mice do not exhibit augmented responses," J. Clin. Invest. 92:1639-49.

Askenase P., et al. (1983) "Defective elicitation of delayed-type hypersensitivty in W/Wv and SI/Sid mast cell deficient mice 1," The Journal of Immunology 6:2687-2693.

Bischoff, S.C., et al. (1992) "c-kit ligand: a unique potentiator of mediator release by human lung mast cells," J. Exp. Med. 175:237-44.

Coleman, J.W., et al. (1993) "Regulation of mouse peritoneal mast cell secretory function by stem cell factor, IL-3 or IL-4," J. Immunol. 150:556-62.

Columbo M., "The human recombinant c-kit receptor ligand," J. of Immunology 149(2)599-608, no date given.

Devinney R., et al. (1990) "Establishment of two dogs mastocytoma cell lines in continuous culture," Am. J. Respr. Cell Mol. Biol. 3:413-420.

Dunn T.B., et al. (1957) "A transplant mast-cell neoplasm in the mouse," J. Natl. Cancer Inst. 18:587-601.

Galli S.J., et al., (1995) "Undiminished immunologic tolerance to contact sensitivity in mast cell-deficient w/wv and sl/s1d mice 1," The Journal of Immunology 2:879-885.

Hirota S., et al. (1998) "Gain of function mutations of c-kit in human gastrointestinal stromal tumors," Science 279:577-580.

Kitayama H., et al. (1995) "Constitutively activating mutations of c-kit receptor tyrosine kinase confer factor-independent growth and tumorigenicity of factor-dependent hematopoietic cell lines," Blood 85:790-798.

Lazarus S.C., et al. (1986) "Isolated canine, mastocytoma cells: propagation and characterization of two cell lines," Am. J. Physiol. 251:C935-944.

Longley, B. "Activating and dominant inactivation c-kit catalytic domain mutations in distinct clinical forms of human mastocytosis," Proc. Natl. Acad. Sci. USA 96(4)1609-14, no date given.

Longley B., "Somatic c-kit activating mutation in urticaria pigmentosa and aggessive mastocytosis" Nature Genetics 12(3)312-314, no date given.

Ma, Y., et al. (1999) "Clustering of activating mutations in c-KIT's juxtamembrance coding region in canine mast cell neoplasms," J. Invest Dermatol 112:165-170.

Ma Y., et al. (1999) "Inhibition of spontaneous receptor phosphorylation by residue in a putative —helix in the KIT intracellular juxtamembrane region," J. Biol. Chem. 274:13399-13402.

Martin F.H., et al. (1990) "Primary structure and functional expression of rat and human stem cell factor DNAs" Cell 63:203-211.

Mohammadi, M., et al. (1997) "Structures of the tyrosine kinase domain of fibroblast growth factor receptor in complex with inhibitors" Science 276:955-960.

Nagata, H., et al. (1995) "Identification of a point of mutation in the catalytic domain of the protooncogene c-kit in peripheral blood mononuclear cells patients who have mastocytosis with an associated hematologic disorder" Proc. Natl. Acad. Sci. USA 92:10560-10564.

Nakajima, K., et al., (1992) "Stem cell factor has histamine releasing activity in rat connective tissue-type mast cell"Biochem. Biophys. Res. Commun. 183:1076-83.

Piao X. et al., (1996) "Onocogene mutation in the kit receptor tyrosine kinase alters substrate specificity and inudes degradation of the protein tyrosine phosphatase SHP-1" Proc. Natl. Acad. Sci. USA 93:14665-14669.

Schrader J.W. et al., (1983) "Delayed Hypersensitivity in Mast-Cell-Deficient Mice" The Journal of Immunology 6:2565-2567.

Sun L. et al., (1998) "Synthesis and biological evaluations of 3-substituted indolin-2-ones: a novel class of tyrosine kinase inhibitors that exhibit selectively toward particular receptor tyrosine kinases" J. Med. Chem. 41:2588-2603.

Tsujimura T. et al., (1994) "Ligand-independent activation of c-kit receptor tyrosine kinase in a murine mastocytoma cell line P-815 generated by a point mutation" Blood 83:2619-2626.

Tsujimura, T. et al., (1996) "Constitutive activation of c-kit in FMA3 murine mastocytoma cells caused bu deletion of seven amino acids at the juxtamembrane domain" Blood 87:273-283.

Wershil, B.K. et al., (1992) "The rat c-kit ligand, stem cell factor, induces c-kit receptor-dependent mouse mast cell activation in vivo. Evidence that signaling through the c-kit receptor can induce expression of cellular function" J. Exp. Med. 175:245-55.

Qiu, F. et al., (1988) "Primary structure of *c-kit*: relationship with the CSF-1/PDGF receptor kinase family-oncogenic activation of *v-kit* involves deletion of extracellular domain and C terminus" EMBO J. 7:1003-1011.

Amendment submitted Aug. 14, 2001 in connection with U.S. Appl. No. 09/474,478, filed Sep. 23, 2002.

Amendment submitted Mar. 4, 2004 in connection with U.S. Appl. No. 09/474,478, filed Dec. 29, 1999.

Amendment submitted Nov. 18, 2002 in connection with U.S. Appl. No. 09/474,478, filed Dec. 29, 1999.

Communication submitted Jan. 16, 2001 in connection with U.S. Appl. No. 09/474,478, filed Dec. 29, 1999.

Communication submitted Jul. 14, 2004 in connection with U.S. Appl. No. 09/474,478, filed Dec. 29, 1999.

Office Action issued Apr. 14, 2004 in connection with U.S. Appl. No. 09/474,478, filed Dec. 29, 1999.

Office Action issued Dec. 4, 2003 in connection with U.S. Appl. No. 09/474,478, filed Dec. 29, 1999.

Office Action issued Feb. 16, 2001 in connection with U.S. Appl. No. 09/474,478, filed Dec. 29, 1999.

Office Action issued Jul. 13, 2000 in connection with U.S. Appl. No. 09/474,478, filed Dec. 29, 1999.

Office Action issued Mar. 31, 2005 in connection with U.S. Appl. No. 09/474,478, filed Dec. 29, 1999.
Office Action issued Sep. 19, 2001 in connection with U.S. Appl. No. 09/474,478, filed Dec. 29, 1999.
Communication submitted Jun. 29, 2005, including Terminal Disclaimer in connection with U.S. Appl. No. 09/474,478, filed Dec. 29, 1999.
Communication submitted Feb. 18, 2005 in connection with U.S. Appl. No. 09/474,478, filed Dec. 29, 1999.
Advisory Action, including Interview Summary issued Jul. 23, 2004 in connection with U.S. Appl. No. 09/474,478, filed Dec. 29, 1999.
Amendment submitted Mar. 17, 2003 in connection with U.S. Appl. No. 09/474,478, filed Dec. 29, 1999.
Advisory Action, including Interview Summary issued Dec. 12, 2002 in connection with U.S. Appl. No. 09/474,478, filed Dec. 29, 1999.
Office Action issued Jul. 16, 2002 in connection with U.S. Appl. No. 09/474,478, filed Dec. 29, 1999.
Advisory Action, including Interview Summary issued Apr. 11, 2002 in connection with U.S. Appl. No. 09/474,478, filed Dec. 29, 1999.
Communication submitted Mar. 19, 2002 in connection with U.S. Appl. No. 09/474,478, filed Dec. 29, 1999.
Amendment filed Dec. 29, 1999 in connection with U.S. Appl. No. 09/474,478, filed Dec. 29, 1999.
Genovese, M.C. et al., (2004) "Combination therapy with etanercept and anakinra in the treatment of patients with rheumatoid arthritis who have been treated unsuccessfully with methotrexate" Arthritis & Rheumatism 50(5)1412-1419.
Verhoeven, A. et al., (1998) "Combination therapy in rheumatoid arthritis: updated systematic review" British Journal of Rheumatology 37:612-619.
Amendment submitted Feb. 4, 2005 in connection with U.S. Appl. No. 09/980,572, filed Sep. 23, 2002.
Communication submitted Jul. 22, 2004 in connection with U.S. Appl. No. 09/980,572, filed Sep. 23, 2002.
Communication submitted Jul. 6, 2000 in connection with PCT International Application No. PCT/US00/12405, filed May 5, 2000.
Office Action issued Jun. 22, 2004 in connection with U.S. Appl. No. 09/980,572, filed Sep. 23, 2002.
Office Action issued Nov. 4, 2004 in connection with U.S. Appl. No. 09/980,572, filed Oct. 31, 2001.
Second Preliminary Amendment filed Feb. 20, 2003 in connection with U.S. Appl. No. 09/980,572, filed Oct. 31, 2001.
Notice of Allowance, including Notice of Allowability which included an Examiner's Amendment and an Interview Summary issued Oct. 28, 2005 in connection with U.S. Appl. No. 09/980,572, filed Sep. 23, 2002.
Communication submitted Jun. 29, 2005, including Terminal Disclaimer in connection with U.S. Appl. No. 09/980,572, filed Sep. 23, 2002.
Office Action issued Nov. 4, 2004 in connection with U.S. Appl. No. 09/980,572, filed Sep. 23, 2002.
Amendment submitted Feb. 25, 2003 in connection with U.S. Appl. No. 09/980,572, filed Sep. 23, 2002.
Amendment submitted Oct. 31, 2001 in connection with U.S. Appl. No. 09/980,572, filed Sep. 23, 2002.
Notification Of Transmittal Of The International Search Report Or The Declaration, including International Search Report mailed Aug. 22, 2000 in connection with PCT International Application No. PCT/US00/12405, filed May 5, 2000.
Notification Regarding Certain Corrections Made *Ex Officio*, mailed Jun. 7, 2000 in connection with PCT International Application No. PCT/US00/12405, filed May 5, 2000.
Notification of Transmittal of International Preliminary Examination Report, including International Preliminary Examination Report mailed Aug. 6, 2001 in connection with PCT International Application No. PCT/US00/12405, filed May 5, 2000.

* cited by examiner

TRANSGENE 1

TRANSGENE 2

FIG. 3A
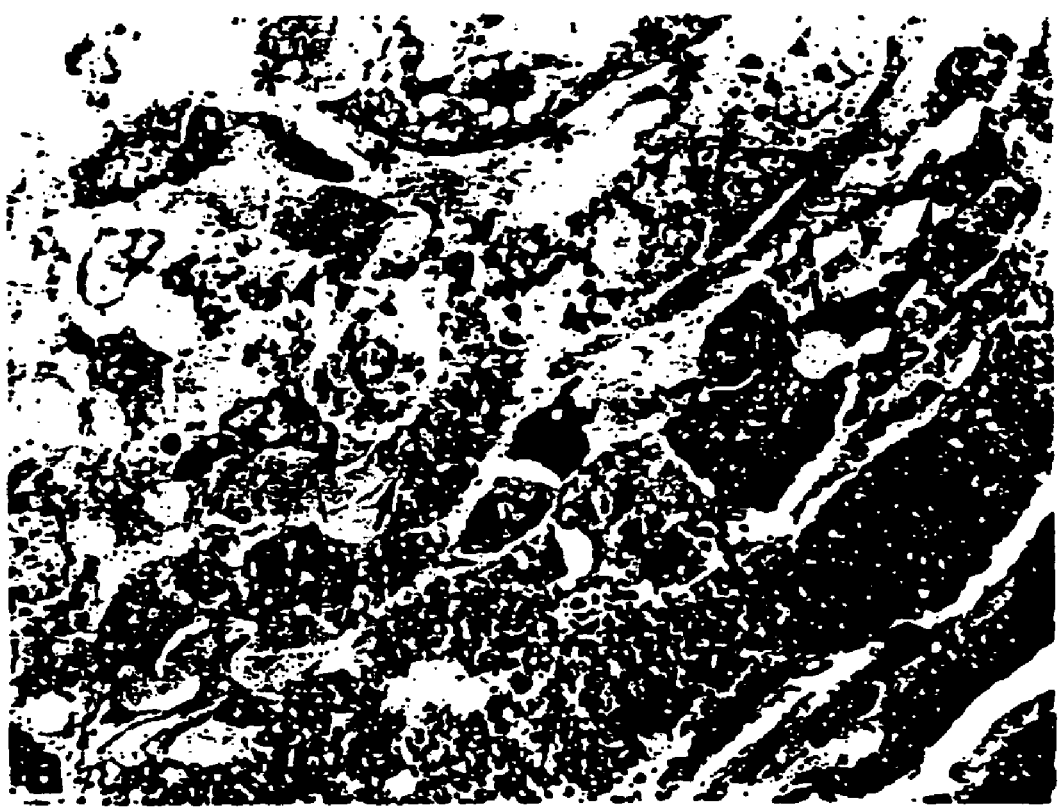
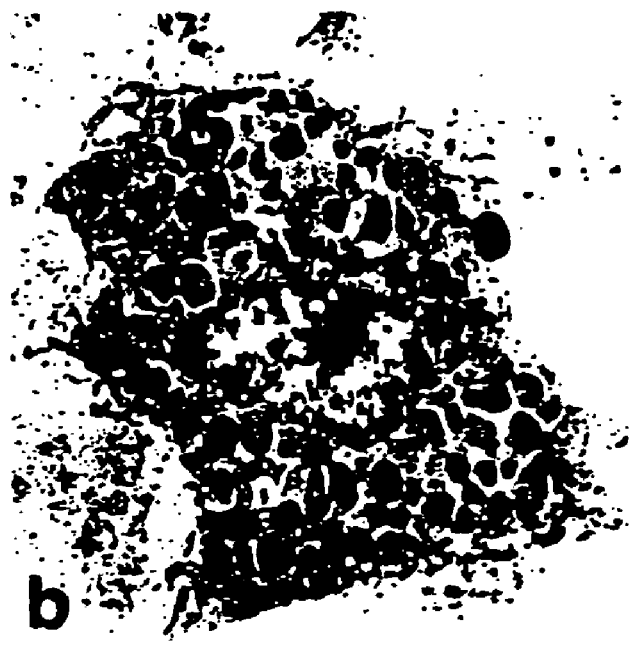
FIG. 3B        FIG. 3C

FIG. 5A
FIG. 5B
FIG. 5C

FIG. 6A
FIG. 6B
FIG. 6C

SEQUENCE LISTING

<160> NUMBER OF SEQ ID NOS: 4

<210> SEQ ID NO 1
<211> LENGTH: 28
<212> TYPE: DNA
<213> ORGANISM: artificial sequence
<220> FEATURE:
<223> OTHER INFORMATION: primer capable of binding to nucleotides
      1568-1593

<400> SEQUENCE: 1 aaatcgcat ccctcacacc ctgttcac                                        28

<210> SEQ ID NO 2
<211> LENGTH: 20
<212> TYPE: DNA
<213> ORGANISM: artificial sequence
<220> FEATURE:
<223> OTHER INFORMATION: primer capable of binding to nucleotides
      1854-1835

<400> SEQUENCE: 2
ccataagcag ttgcctcaac                                                20

<210> SEQ ID NO 3
<211> LENGTH: 20
<212> TYPE: DNA
<213> ORGANISM: artificial sequence
<220> FEATURE:
<223> OTHER INFORMATION: primer capable of binding to nucleotides

```
        2384-2403

<400> SEQUENCE: 3
tgtattcaca gagacttggc                                                    20

<210> SEQ ID NO 4
<211> LENGTH: 20
<212> TYPE: DNA
<213> ORGANISM: artificial
<220> FEATURE:
<223> OTHER INFORMATION: primer capable of binding to nucleotides
      2595-2576

<400> SEQUENCE: 4
aaaatcccat aggaccagac                                                    20
```

US 7,449,309 B2

METHODS FOR DESENSITIZING A SUBJECT TO AN AGENT

This application is a continuation of U.S. Ser. No. 09/980,572, filed Sept. 23, 2002, now U.S. Pat. No. 6,977,159 B1, issued Dec. 20, 2005, §371 national stage of PCT International Application No. PCT/US00/12405, filed May 5, 2000 and designating the United States of America, which is a continuation-in-part and claiming priority of U.S. Ser. No. 09/474,478, filed Dec. 29, 1999, now U.S. Pat. No. 6,989,248 B2, issued Jan. 24, 2006, which is a continuation-in-part of U.S. Ser. No. 09/306,143, filed May 6, 1999, now U.S. Pat. No. 6,576,812 B1, issued Jun. 10, 2003, the contents of each of which are hereby incorporated by reference into this application.

The invention described herein was made with Government support under grant numbers 1 R29 AR 40514-01A1, 5 P30 041942 and 1-RO1-AR43356-01A2 from the National Institutes of Health. Accordingly, the United States Government has certain rights in this invention.

Throughout this application, various publications are referenced by Arabic numerals within parentheses. Disclosures of these publications in their entireties are hereby incorporated by reference into this application to more fully describe the state of the art to which this invention pertains. Full bibliographic citations for these references may be found immediately preceding the claims.

BACKGROUND OF THE INVENTION

The use of marine models to investigate human coetaneous oncology, immunology and keratinocyte biology is advantageous over the use of human skin for obvious reasons. However, substantial differences exist between human skin and marine skin. In human skin, Stem Cell Factor is produced by epidermal keratinocytes after birth, unlike in normal marine skin. The result of this, among other things, is that melanocytes are present in the interadnexal epidermis in human skin. In contrast, melanocytes in adult marine skin are generally confined to hair follicles, with the exception of rare epidermal melanocytes found in the ears, footpads, and tail (1). A few dermal melanocytes may also be found in mice, mostly in the ears. These differences have compromised the use of the mice as a model system for investigation of human coetaneous biology.

It has been discovered that melanocyte migration and development, as well as the survival of melanocytes and mast cells, are dependent on expression of the kit protein, a receptor tyrosine kinas encoded by the c-kit proto-oncogene (2-6). The ligand for kit, known as stem cell factor (SCF) (also called mast cell growth factor, steel factor, and kit ligand) may be produced locally in human skin by epidermal keratinocytes, fibroblasts, and endothelial cells (7-8). However, definitive studies of SCF production in marine skin have not been reported. Transgenic studies using the SCF gene promoter region and beta-glycosidase as a reporter gene suggest that, unlike in human skin, postnatal marine coetaneous SCF expression is limited to the dermis and hair follicles, and not found in epidermal keratinocytes (9). The difference in SCF expression between human and marine epidermis could explain the difference in melanocyte distribution and other biological phenomena in these two species.

SCF may be produced in two is forms by alternate splicing of axon 6. One is form lacks axon 6 encoded sequences and exists predominantly as a membrane-bound molecule. The other is form contains axon 6 encoded sequences which include a protease sensitive site (10-19). Cleavage at the protease sensitive site causes the release of a soluble, bioactive form of SCF. The membrane-bound and soluble forms of SCF have differential effects on melanocyte precursor dispersal and survival (20) and exogenous soluble SCF may produce coetaneous mast cell hyperplasia and coetaneous hyper pigmentation (21-23). In addition, local high concentrations of soluble SCF have been found in lesions of human coetaneous mastocytosis, a disease characterized by dermal accumulations of mast cells and increased epidermal melanin (7, 8, 24) and in spongiotic dermatitis, a common inflammatory condition of human skin (our unpublished data).

SUMMARY OF THE INVENTION

This invention provides a method of preventing or treating in a subject contact dermatitis which comprises administering to the subject an amount of a compound capable of inhibiting the stem cell factor signaling pathway effective to prevent or treat contact dermatitis so as to thereby prevent or treat contact dermatitis in the subject.

This invention provides a method of preventing or treating in a subject hyper pigmentation which comprises administering to the subject an amount of a compound capable of inhibiting the stem cell factor signaling pathway effective to prevent or treat hyper pigmentation so as to thereby prevent or treat hyper pigmentation in the subject.

This invention provides a method of preventing or treating in a subject asthma which comprises administering to the subject an amount of a compound capable of inhibiting the stem cell factor signaling pathway effective to prevent or treat asthma so as to thereby prevent or treat asthma in the subject.

This invention provides a method of preventing or treating in a subject coetaneous inflammation which comprises administering to the subject an amount of a compound capable of inhibiting the stem cell factor signaling pathway effective to prevent or treat coetaneous inflammation so as to thereby prevent or treat coetaneous inflammation in the subject.

This invention provides a method of preventing or treating in a subject anaphylaxis and bronchospasm which comprises administering to the subject an amount of a compound capable of inhibiting the stem cell factor signaling pathway effective to prevent or treat anaphylaxis and bronchospasm so as to thereby prevent or treat anaphylaxis and bronchospasm in the subject.

This invention provides a method of preventing or treating in a subject mastocytosis which comprises administering to the subject an amount of a compound capable of inhibiting the stem cell factor signaling pathway effective to prevent or treat mastocytosis so as to thereby prevent or treat mastocytosis in the subject.

This invention provides a method of preventing or treating in a subject urinary which comprises administering to the subject an amount of a compound capable of inhibiting the stem cell factor signaling pathway effective to prevent or treat urinary so as to thereby prevent or treat urinary in the subject.

This invention provides a method of preventing or treating in a subject hypersensitivity reactions which comprises administering to the subject an amount of a compound capable of inhibiting the stem cell factor signaling pathway effective to prevent or treat hypersensitivity reactions so as to thereby prevent or treat hypersensitivity reactions in the subject.

This invention provides a method of preventing or treating in a subject airway inflammation which comprises administering to the subject an amount of a compound capable of inhibiting the stem cell factor signaling pathway effective to prevent or treat airway inflammation so as to thereby prevent or treat airway inflammation in the subject.

This invention provides a method of preventing or treating in a subject interstitial cystitis which comprises administering to the subject an amount of a compound capable of inhibiting the stem cell factor signaling pathway effective to prevent or treat interstitial cystitis so as to thereby prevent or treat interstitial cystitis in the subject.

This invention provides a method of preventing or treating in a subject a tumor which expresses activated kit which comprises administering to the subject an amount of a compound capable of inhibiting the stem cell factor signaling pathway effective to prevent or treat a tumor which expresses activated kit so as to thereby prevent or treat a tumor which expresses activated kit in the subject.

The invention provides a method of providing contraception to a subject which comprises administering to the subject an amount of a compound capable of inhibiting the stem cell factor signaling pathway effective to prevent conception so as to thereby provide contraception to the subject.

This invention provides a method of desensitizing a subject to an agent which comprises administering to the subject an amount of a compound capable of inhibiting the stem cell factor signaling pathway effective to desensitize the subject to the agent so as to thereby desensitize the subject to the agent.

Figure 1A:
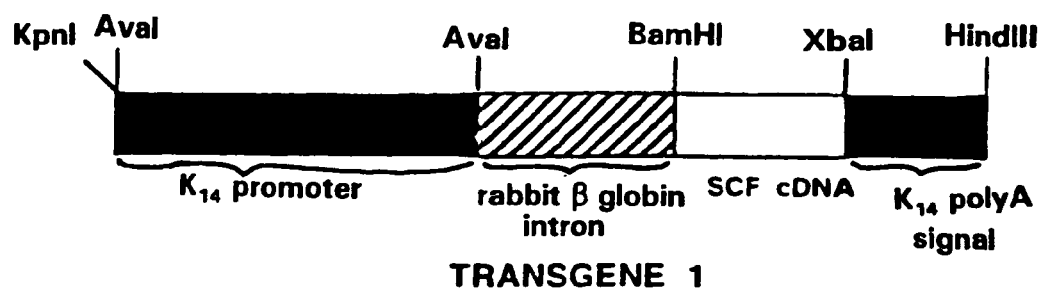
FIG. 1.

Transgenic design. Both transgenic used the human keratin 14 promoter and polyadenylation sequences. Transgenic one included a rabbit b-globin intone, and transgenic two included human growth hormone sequences to provide for stability.

Neither the beta globin intone nor the human growth hormone sequences produce protein products.

FIG. 2:

Increased mast cells in mice expressing epidermal membrane and soluble SCF (transgenic one). (a) Numerous mast cells are demonstrated in the superficial dermis of body wall skin of newborn mice bearing transgenic one (membrane/soluble SCF), using an immunoperoxidase/alcian blue technique which stain mast cell granules met achromatically purple. Note the apposition of mast cells (arrowheads) to basilar keratinocytes, the source of SCF. Immunoperoxidase with an anti-S100 antibody in this preparation also demonstrates melanocytes as brown staining cells in the epidermal basilar layers of epidermis and follicles (white arrows). Sebocytes are seen as large, round, lightly S-100(+) cells in the follicular epithelium. Melanin pigment is stained black in this preparation. (b) Immunofluorescence with anti-kit antibodies highlights kit expressing dermal mast cells (arrowheads) in body wall skin of newborn (transgenic one membrane/soluble SCF) mouse. (c) Anti-kit antibody immunofluorescence shows mast cells crowded in the papillary dermis and extending into the upper reticular dermis and body wall skin of 21 day old, transgenic one positive mouse, MC, confluent mast cells; arrowheads, individual and small clusters of mast cells; E, epidermis; F, follicles; K, keratin layer. (d) Hematoxylin and eosin-stained sections show mast cells filling the superficial corium in section of tongue from a 21 day old, transgenic one positive mouse. The lack of abundant melanocytes and melanophages in this anatomic site allows easy visualization of the mast cells. This histological picture is identical to that seen in human coetaneous mastocytosis. (e) Alcian blue stained serial section of tongue shows metachromatic granules in mast cells of 21 day old, transgenic one positive mouse.

FIG. 3:

Electron microscopy confirms the presence of melanocytes and mast cells in transgenic mice. (a) Transgenic one mouse with membrane/soluble epidermal SCF has numerous dermal mast cells (arrowheads) as well as dermal melanocytes (arrows). Asterisks show the boundary of the dermis and hair follicle. Higher magnification images of mast cell and melanocyte are shown in b and c, respectively. Original magnifications: (a) 2,750, (b) 9,000, (c) 11,750.

FIG. 4:

Transgenic phenotypes are stable across a wide range of gene expression levels. This figure compares the transgenic copy number determined by PCR, with SCF mRNA expression as determined by RNAse protection assay, in lines from different founders. The relative density of SCF bands was determined by dividing the mean density of the SCF band by the density of a SCF band derived from an identical aliquot of RNA. Probe templates were 384 bases in length for SCF (40 base pairs of promoter sequence and 342 bases complimentary to nucleotides 814-1156 of marine SCF mRNA (5). A beta-actin probe was used as a control, and to allow standardization between RNA preparations from different mice. The beta-actin probe length was 310 bases, 227 bases of which are complementary to marine beta-actin mRNA. The probe was purchased from Ambion (pTR1-beta-actin-mouse anti-sense control template). Note the differences between TG2 (4×, 5×, 10×) and TG1 (6×).

FIG. 5:

Epidermal SCF causes hyper pigmentation of marine skin. (a) Newborn mouse expressing membrane/soluble SCF (transgenic one, left) shows obvious hyper pigmentation compared to non-transgenic littermate (right). (b) Transgenic two positive mouse over expressing membrane-bound epidermal SCF shows a similar phenotype with generalized hyper pigmentation which is most discernible in the ventral and hairless areas, and which is maintained in adult life. Three week old transgenic (left) and non-transgenic littermate (right)

FIG. 6:

Intraepidermal melanocytes are increased in transgenic mice. (a) Tail skin section from 21 day old mouse expressing epidermal membrane-bound SCF (transgenic two) shows mild epidermal hyperplasia and a markedly increased number of melanocytes, identified as cells surrounded by clear halos, mostly at the dermal-epidermal junction. These mice also show extensive black epidermal melanin pigment (400×). (b) Note the lack of both basilar melanocytes and epidermal pigment in the skin of the transgenic (−) littermate control mouse (C57 black 6 (400×)). (c) Epidermal melanocytes express kit protein. Immunofluorescence staining with anti-kit antibody and Texas Red labeled secondary antibody demonstrates confluent dendrite cells in the epidermal basilar layer of mice expressing membrane-bound SCF (transgenic two arrows). These cells correspond to the S-100 protein (+) basilar dendrite cells seen in FIG. 2a. Note two strongly kit positive solitary mast cells in the dermis (arrowheads, 400×). Light staining of dendrite melanocytes can also be seen in the epidermis of transgenic one positive mice (please see FIG. 2b).

FIG. 7:

Electron microscopy confirms the presence of epidermal melanocytes in both types of transgenic mice. (a) Electron microscopy shows numerous keratinocytes containing phagocytes melanin granules in the interadnexal epidermis of mice expressing membrane-bound epidermal SCF (3500×).
b. Epidermal melanosomes, some marked with large arrows, are present in both keratinocytes and melanocytes. Pre melanosomes, marked with the open arrows, demonstrate the presence of a melanocyte. Note keratinocyte hemidesmosomes (small arrows) which confirm the location of the melanocyte within the epidermis (16, 320×).

FIG. 8:

Allergic ear swelling is significantly increased in SCF transgenic animals, and is reduced by blocking the SCF receptor with the ACK2 monoclonal antibody. All transgenic mice show increased ear swelling in response to allergic contactants compared to non-transgenic animals ($p \leq 0.0001$), showing that SCF contributes to dermatitis. Similar results are seen with irritant contactants (data not shown). The ear swelling is specifically decreased by the ACK2 monoclonal antibody which blocks the SCF receptor ($p \leq 0.05$) confirming that epidermal SCF plays an active role in cutaneous inflammation.

FIG. 9:

(a) An unpublished immunoperoxidase study of inflamed human skin with an anti-human SCF monoclonal anti-body shows soluble epidermal SCF in spongiotic (eczematous) dermatitis, here demonstrated in an epidermal spongiotic vesicle. Human spongiotic dermatitis may be associated with hyperpigmentation. Soluble epidermal SCF is not detected in normal skin with this technique (7), suggesting that epidermal SCF is released in cutaneous inflammatory states. (b) Irritant dermatitis induced in transgenic mice by Croton oil is characterized histologically by spongiotic (eczematous) dermatitis. The marine dermatitis is shown in a hematoxylin and eosin stained slide because no satisfactory antibody against marine SCF is available to allow demonstration of soluble SCF by immunoperoxidases. However, these results combined with the ACK2 blocking studies shown above implicate epidermal SCF in this phenomenon.

FIG. 10:

Ear swelling response to croton oil in the 4202 (1×) strain of epidermal SCF transgenic mice. Significance levels by Mann-Whitney U Test.

FIG. 11:

Ear swelling response of the 4197 (1×) strain of transgenic mice. Significance levels use Mann-Whitney U test. Results are even more significant if analyzed by ANOVA with a mixed effects model ($p<0.001$).

FIG. 12:

Irritant dermatitis caused by croton oil is decreased by blocking KIT signaling with anti-KIT monoclonal antibody, as evidenced by decreased ear welling in 4197 (1×) SCF transgenic mice. $P<0.02$ by ANOVA with mixed effects models. Please note that the ear swelling of 0.02 mm at 48 hours in the KIT inhibited group is statistically identical to that of the non-transgenic mice (not treated with antibody, see FIG. 10).

FIG. 13:

Effect of ACK2 on the 24-hour passive cutaneous anaphylaxis (PCA) in mice. Each amount of dye represents the mean±S.E. of 4 experiments. Treatment with saline measured O.D. of extracted dye at 0.0075±0.0015. Treatment with Anti-DNP IgE measured O.D. of extracted dye at 0.0587±0.0096*. Treatment with Control IgG+Anti-DNP IgE measured O.D. of extracted dye at 0.0571±0.0064°. Treatment with ACK2+ Anti-DNP IgE measured O.D. of extracted dye at 0.0223±0.0049.

$p<0.01$ vs. Saline group.

$p<0.01$ vs. anti-DNP IgE group.

DETAILED DESCRIPTION OF THE INVENTION

This invention provides a method of preventing or treating in a subject contact dermatitis which comprises administering to the subject an amount of a compound capable of inhibiting the stem cell factor signaling pathway effective to prevent or treat contact dermatitis so as to thereby prevent or treat contact dermatitis in the subject.

This invention provides a method of preventing or treating in a subject hyperpigmentation which comprises administering to the subject an amount of a compound capable of inhibiting the stem cell factor signaling pathway effective to prevent or treat hyperpigmentation so as to thereby prevent or treat hyperpigmentation in the subject.

This invention also provides a method of preventing or treating spongiotic dermatitis which comprises administering to the subject an amount of a compound capable of inhibiting the stem cell factor signaling pathway effective to prevent or treat spongiotic dermatitis so as to thereby prevent or treat spongiotic dermatitis in the subject. As used herein, "spongiotic dermatitis" includes but is not limited to contact dermatitis.

This invention provides a method of preventing or treating in a subject asthma which comprises administering to the subject an amount of a compound capable of inhibiting the stem cell factor signaling pathway effective to prevent or treat asthma so as to thereby prevent or treat asthma in the subject.

This invention provides a method of preventing or treating in a subject cutaneous inflammation which comprises administering to the subject an amount of a compound capable of inhibiting the stem cell factor signaling pathway effective to prevent or treat cutaneous inflammation so as to thereby prevent or treat cutaneous inflammation in the subject.

This invention provides a method of preventing or treating in a subject anaphylaxis and bronchospasm which comprises administering to the subject an amount of a compound capable of inhibiting the stem cell factor signaling pathway effective to prevent or treat anaphylaxis and bronchospasm so as to thereby prevent or treat anaphylaxis and bronchospasm in the subject.

This invention provides a method of preventing or treating in a subject mastocytosis which comprises administering to the subject an amount of a compound capable of inhibiting the stem cell factor signaling pathway effective to prevent or treat mastocytosis so as to thereby prevent or treat mastocytosis in the subject.

This invention provides a method of preventing or treating in a subject urinary which comprises administering to the subject an amount of a compound capable of inhibiting the stem cell factor signaling pathway effective to prevent or treat urinary so as to thereby prevent or treat urinary in the subject.

This invention provides a method of preventing or treating in a subject hypersensitivity reactions which comprises administering to the subject an amount of a compound capable of inhibiting the stem cell factor signaling pathway effective to prevent or treat hypersensitivity reactions so as to thereby prevent or treat hypersensitivity reactions in the subject.

This invention provides a method of preventing or treating in a subject airway inflammation which comprises administering to the subject an amount of a compound capable of inhibiting the stem cell factor signaling pathway effective to prevent or treat airway inflammation so as to thereby prevent or treat airway inflammation in the subject. In one embodiment, the airway inflammation is rhinitis. In another embodiment, the airway inflammation is sinusitis.

This invention provides a method of preventing or treating in a subject interstitial cystitis which comprises administering to the subject an amount of a compound capable of inhibiting the stem cell factor signaling pathway effective to prevent or treat interstitial cystitis so as to thereby prevent or treat interstitial cystitis in the subject. As sued herein, "interstitial cystitis" includes bladder inflammation.

This invention provides a method of preventing or treating in a subject a tumor which expresses activated kit which comprises administering to the subject an amount of a compound capable of inhibiting the stem cell factor signaling pathway effective to prevent or treat a tumor which expresses activated kit so as to thereby prevent or treat a tumor which expresses activated kit in the subject.

In one embodiment, the tumor is a mast cell tumor. In another embodiment, the tumor is a gastrointestinal stromal tumor. In another embodiment, the tumor is a germ cell tumor.

In one embodiment, the above method comprises inhibiting the kinas enzymatic reaction of kit protein.

In one embodiment, the above method comprises inhibiting chymase, lactase or other SCF cleaving enzymes.

In one embodiment, the above method comprises inhibiting ligand binding with an antibody, peptide, or nonpeptide chemical.

In one embodiment, the above method comprises inhibiting receptor dimerization with an antibody, peptide, or nonpeptide chemical.

In one embodiment of the above method, downstream signaling of the kit activation pathway is inhibited by blocking substrate association with the kit kinas domain.

In one embodiment of the above method, downstream signaling of the kit activation pathway is inhibited by blocking enzymatic function in the downstream signaling pathway.

In one embodiment of the above method, downstream signaling of the kit activation pathway is inhibited by blocking binding of molecules in the downstream signaling pathway.

In one embodiment of the above method, the compound is an antibody or portion thereof. In one embodiment, the antibody is a monoclonal antibody. In one embodiment, the monoclonal antibody is a human, humanized or a chimerical antibody. In one embodiment, the monoclonal antibody is an anti-kit antibody. In one embodiment, the anti-kit antibody is ACK2.

This invention provides the above method, wherein the compound comprises a Fab fragment of an anti-kit antibody.

This invention provides the above method, wherein the compound comprises the variable domain of an anti-kit antibody.

This invention provides the above method, wherein the compound comprises one or more CDR portions of an anti-kit antibody.

This invention provides the above method, wherein the antibody is selected from the group consisting of IgA, IgD, IgE, IgG and IgM.

This invention provides the above method, wherein the compound comprises a peptide, peptidomimetic, a nucleic acid, or an organic compound with a molecular weight less than 500 Daltons.

This invention provides the above method, wherein the compound is sSCF, SKIT ligand or a fragment thereof. As used herein "sSCF" can also mean "SKIT ligand."

This invention provides the above method, wherein the compound is sKIT or a fragment thereof.

This invention provides the above method, wherein the subject is a mammal. The subject of the above methods includes but is not limited to a mammal. The subject may be a mammal or non-mammal. The subject may be a human, a primate, an equine subject, an opine subject, an avian subject, a bovine subject, a porcine, a canine, a feline or a marine subject. In another embodiment, the subject is a vertebrate. In a preferred embodiment, the mammal is a human being.

This invention provides the above method, wherein the administration is intralesional, intraperitoneal, intramuscular, subcutaneous, intravenous, liposome mediated delivery, transmucosal, intestinal, topical, nasal, oral, anal, ocular or optic, intravascular, or potential delivery.

This invention provides a method of providing contraception to a subject which comprises administering to the subject an amount of a compound capable of inhibiting the stem cell factor signaling pathway effective to prevent conception so as to thereby provide contraception to the subject. In one embodiment, the subject is a male subject. In another embodiment, the subject is a female subject.

This invention provides the above method which comprises inhibiting the kinas enzymatic reaction of kit protein.

This invention provides the above method comprises inhibiting chymase, lactase or other SCF cleaving enzymes.

This invention provides a method of desensitizing a subject to an agent which comprises administering to the subject an amount of a compound capable of inhibiting the stem cell factor signaling pathway effective to desensitize the subject to the agent so as to thereby desensitize the subject to the agent.

For example, the agent can be one which causes an allergic or other immune response in a subject. Examples of agents include but are not limited to workplace chemicals or pollens.

One skilled in the art can employ various methods for determining whether a compound inhibits the stem cell signaling pathway. One of these methods comprises:
  a) immobilizing kit protein on a solid matrix;
  b) contacting the immobilized kit protein with the compound being tested and a predetermined amount of SCF under conditions permitting binding of kit protein and SCF in the absence of the compound;
  c) removing any unbound compound and any unbound SCF;
  d) measuring the amount of SCF which is bound to the immobilized kit protein;
  e) comparing the amount measured in step (d) with the amount measured in the absence of the compound, a decrease in the amount of SCF bound to the kit protein in the presence of the compound indicating that the compound inhibits binding of SCF to kit protein, thereby indicating that the compound inhibits the stem cell factor signaling pathway.

Another method includes detecting in vitro phosphorylation of kit comprising the following steps:
  1. Cells expressing KIT, either naturally occurring as in the C2, BR, P815, or HMC1 lines, or as the result of DNA transfection, are grown in vitro in the absence of exogenous SCF.
  2. The cells are treated with the compound or substance. In the case of cells expressing wild type (non-mutated and not constructively activated) KIT, treatment with the substance or compound may be followed by treatment with SCF. Controls include cells treated with compound or substance, and not exposed to SCF.
  3. The cells are lyses and KIT is immunoprecipitated, electrophoresed, blotted with anti-phosphotyrosine antibody, and the antibody detected by chemiluminescence or radioactive labeling and autoradiography, thereby determining the level of KIT phosphorlyation on tyrosine.
  4. The level of KIT phosphorlyation on tyrosine in cells not exposed to the compound or substance is compared to KIT phosphorlyation on tyrosine in cells exposed to the compound or substance. A decrease in KIT phosphorlyation on tyrosine in the treated cells indicates that the compound or substance inhibits the SCF signaling pathway.

A cell proliferation and viability method comprises the following steps:
1. Cells expressing KIT, and depending on KIT activation for survival, are grown in the presence of SCF if they express wild type KIT or in the absence of SCF if they express mutated and constructively activated KIT.
2. The cells are grown in replicate tissue culture wells, in the presence or absence of the compound or substance to be tested, and the number of viable and non-viable cells per well is determined daily by counting a sample of cells in a hemocytometer. The number of viable and non-viable cells are determined by the trepan blue exclusion method.
3. A decrease in cell growth, as determined by the presence of fewer viable cells in the wells treated with the compound or substance compared to the cells in the wells not so treated, indicates that the compound or substance interferes with the KIT SCF signaling pathway.
4. Alternatively, cell growth may be determined by measuring cellular incorporation of labeled substances such as tritium labeled thymidine.

The present invention provides a method of identifying a composition, a compound or a procedure which can produce a skin response in a subject, comprising: a) administering said composition or compound, or applying said procedure to the transgenic mice which express endogenous epidermal stem cell factor, and b) analyzing the contacted skin for response.

In one embodiment of the method, the composition or compound can be administered orally or by injection.

In another embodiment of the method, the composition or compound can be administered topically by contacting the composition or compound with the skin of the transgenic mice.

In another embodiment of the method, the procedure is not previously known.

In another embodiment of the method, the procedure is identified by the method.

In another embodiment of the method, the procedure is DNA vaccination.

In this invention, the skin response may be induced. This skin response includes but is not limited to inflammation, tanning, melanoma, carcinoma or hyperpigmentation.

In another embodiment of the method, the composition may be cosmetics, medications or skin care products.

In another embodiment of the method, the composition or compound is not previously known.

In yet another embodiment of the method, the composition or compound is identified by the method.

In a further embodiment of the method, a mixture is produced for producing a skin response comprising an effective amount of the composition or compound identified by the method and a suitable carrier.

The present invention also provides a method of identifying a composition, a compound, or a procedure which can reduce or treat skin response in a subject, comprising: a) administering said composition or compound, or applying said procedure to the transgenic mice which express endogenous epidermal stem cell factor and which had been induced to produce a skin response and b) analyzing the skin of said transgenic mice to determine the reduction of skin response, wherein the reduction of skin response indicates that the composition, compound, or procedure can reduce skin response.

In one embodiment of the method, the composition or compound can be administered orally or by injection.

In another embodiment of the method, the composition or compound can be administered topically by contacting the composition or compound with the skin of the transgenic mice.

In another embodiment of the method, the procedure is not previously known.

In another embodiment of the method, the procedure is identified by the method.

In another embodiment of the method, the procedure is DNA vaccination.

In another embodiment of the method, the composition or compound is not previously known.

In another embodiment of the method, the composition or compound is identified by the method.

In another embodiment of the method, a mixture is produced for reducing skin response comprising an effective amount of the composition or compound identified by the method and a suitable carrier.

In another embodiment of the method, the skin response is inflammation, tanning, skin carcinoma, melanoma or hyperpigmentation.

In another embodiment of the method, the hyperpigmentation is natural occurring hyperpigmentation or post inflammatory hyperpigmentation.

In another embodiment of the method, the inflammation is associated with human hyperpigmentation, or human hypo pigmentation.

In another embodiment of the method, the subject is a mouse or a human-being.

In another embodiment of the method, the epidermal stem cell factor transgenic encodes either a membrane bound epidermal stem cell factor or a membrane/soluble epidermal stem cell factor.

In another embodiment of the method, the epidermal stem cell factor transgenic encodes a membrane or soluble epidermal stem cell factor.

In another embodiment of the method, the epidermal stem cell factor transgenic is cloned into a construct containing a human cytokeratin 14 promoter.

In another embodiment of the method, the human cytokeratin 14 promoter causes the expression of the stem cell factor transgenic in marine skin of the basal layers of the interadnexal epidermis and the follicular epithelium.

In another embodiment of the method, the skin response of the transgenic mice can be induced by applying an irritant or an allergic dermatitis inducing agent to said skin.

In another embodiment of the method, the irritant is croton oil or dinitrofluorobenzene.

In another embodiment of the method, the croton oil or dinitrofluorobenzene are applied to the ear or the abdominal skin of the transgenic mice; wherein the abdominal skin is either hairless or shaved.

In another embodiment of the method, the croton oil is used at a concentration of 0.2 percent.

In another embodiment of the method, the dinitrofluorobenzene is used at a concentration of 0.5 percent in a 4:1 mixture of acetone and olive oil.

In another embodiment of the method, the reduction or treatment of hyperpigmentation is determined by electron microscopic analysis.

In another embodiment of the method, the compound is an epidermal stem cell factor inhibitor.

In yet another embodiment of the method, the stem cell factor inhibitor is a monoclonal antibody.

In a further embodiment of the method, the monoclonal antibody is ACK2.

The present invention further provides a method of identifying a composition, a compound or a procedure which can reduce radiation damage to the skin of a subject, comprising: a) administering said composition or compound, or applying said procedure to the transgenic mice which express endogenous epidermal stem cell factor, b) subjecting the skin of said transgenic mice and the skin of the control transgenic mice to radiation, and c) analyzing the effects of said composition, compound, or procedure on reducing skin radiation damages.

In one embodiment of the method, the composition or compound can be administered orally or by injection.

In another embodiment of the method, the composition or compound can be administered topically by contacting the composition or compound with the skin of the transgenic mice.

In another embodiment of the method, the procedure is not previously known.

In another embodiment of the method, the procedure is identified by the method.

In another embodiment of the method, the procedure is DNA vaccination.

In another embodiment of the method, the composition or compound is not previously known.

In another embodiment of the method, the composition or compound is identified by the method.

In another embodiment of the method, a mixture is produced for reducing skin radiation damages comprising an effective amount of the composition or compound identified by the method and a suitable carrier.

In yet another embodiment of the method, the radiation is ultra-violet light.

In a further embodiment of the method, the radiation damage is tanning, carcinogenesis, photo-aging, photo-damage or the development of melanoma.

The present invention also provides a pharmaceutical composition for treating human skin diseases, comprising (a) a compound that can treat skin diseases of the transgenic mice which express endogenous epidermal stem cell factor, and (b) a suitable carrier, wherein the compound specifically targets the epidermal stem cell factor or its receptor.

In one embodiment of the pharmaceutical composition, the compound is ACK2.

This invention will be better understood from the Experimental Details which follow. However, one skilled in the art will readily appreciate that the specific methods and results discussed are merely illustrative of the invention as described more fully in the claims which follow thereafter.

Experimental Details

Figure 1B:
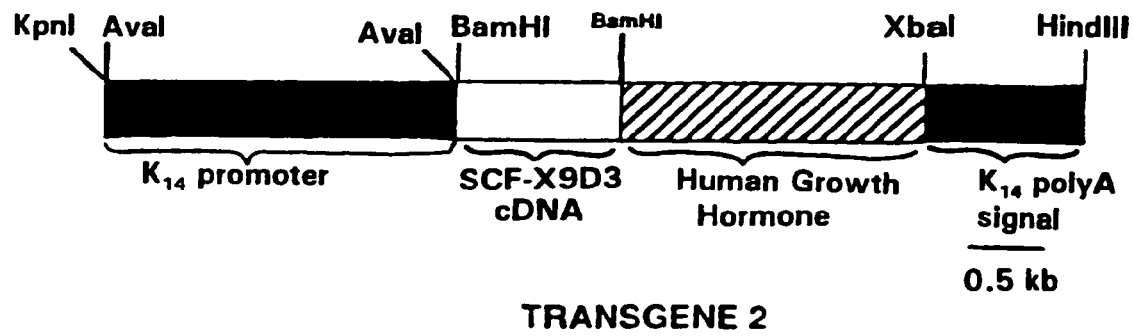

Transgenic Construction:

Two marine SCF cDNAs were cloned into constructs containing the human cytokeratin 14 upstream region (27) (FIG. 1). This promoter causes expression in the skin limited to the basal layers of the interadnexal epidermis and the follicular epithelium. The cDNAs were both full length clones, containing axon 6 encoded sequences. One cDNA (transgenic one) was unmodified and therefore could produce a membrane-bound protein with the axon 6 encoded protease sensitive site, from which a soluble, bioactive form of SCF could be efficiently generated (10, 11, 28). The product of this transgenic will be referred to as membrane/soluble SCF. The second cDNA (transgenic two) had been previously modified by site directed mutagenesis, deleting the primary high efficiency cleavage site (between amino acids 164 and 165) and an alternate axon 7 encoded low efficiency cleavage site (found in marine SCF between amino acids 180 and 181). The SCF produced by this transgenic therefore exists predominantly as a membrane-bound molecule (membrane SCF) (29). Both cDNAs have been previously shown to produce biologically active SCF (29, 30).

Generation and Analysis of Transgenic Animals:

Two μg/ml transgenic DNA, in 10 mM Tris (pH 7.5), 01.mM EDTA was injected into fertilized acolytes collected from pseudopregnant mice as described (31). At birth, most transgenic expressing mice could be identified by distinctive pigmentary phenotypes, as described in the Results section. Integration of transgenic was verified by polymerase chain reaction (PCR) of genomic DNA with transgenic-specific primers and copy number estimated by Southern blotting of POR products, followed by autoradiography and densitometry. Skin specific expression of transgenic messenger RNA was confirmed by northern blotting and by reverse transcription-polymerase chain reaction with transgenic specific primers using RNA extracted from representative animals. Transgenic expression was guantitated by RPA II Ribonuclease Protection Assay Kit (Ambion, Austin TX, USA) according to the manufacturer's directions. Briefly, total RNA extracted from mouse skin was hybridized with digoxigenin labeled single stranded RNA probes for twenty three hours at 42° C, digested with RNAse A and RNAse T1, electrophoresed through 5% polyacrylamide/7 Molar urea, protected fragments were transferred to $Hy^{30}$ membrane (Boerheringer-Mannheim, Indianapolis, IN, USA), bands detected by chemiluminescences, and band density determined by densitometry. Preliminary studies of RNA preparations from each transgenic line were performed to measure Betaactin, and the amounts of RNA for SCF mRNA determinations adjusted for comparison. RNA was also used with reverse transcription and the polymerase chain reaction for direct applier sequencing of c-kit mRNA sequences in regions which could contain known activating mutations, as previously described (25). The primers used were 5' CAAATC/GCATCCC/TCA-CACCCTGTTCAC (SEQ. ID. NO:1) and 5' CCATAAG-CAGTTGCCTCAAC (SEQ. ID. NO:2) which binds to nucleotides 1568-1593 and 1854-1835 and 5' TGTATTCACAGAGACTTGGC (SEQ. ID. NO:3) and 5' AAAATCCCATAGGACCAGAC (SEQ. ID. NO:4) binding to nucleotides 2384-2403 and 2595-2576. These regions contain the cordons with both of the activating mutations, cordon 559 and cordon 814, respectively which have been described in human mastocytosis and in a marine mast cell line (5, 26)

Transgenic one, containing the full-length unmodified SCF cDNA (membrane/soluble SCF), was injected into 100 F1 acolytes (C57 BL6×SLJ), which were implanted into six host mothers, resulting in four independent hyper pigmented mice, all of which were positive for the transgenic, and 40 other littermates which were pigmentary phenotype negative and transgenic negative by PCR.

Acolytes for transgenic two (membrane SCF) were F1 (CS7BL/6J female×SLJ/J male), and the offspring could be black, agouti, or white. Injection of 40 embryos and implantation into six host mothers generated 48 pups, 21 of which were positive for integration by PCR. Of the 25 founder mice identified by PCR with the transgenic specific primers, 3 were black, 13 were agouti, and 9 were white. Five PCR positive mice (3 agouti and 2 black) showed a clearly identifiable pigmentary phenotype. Given the inability of white mice to produce normal cutaneous pigment, it is possible that there were also white founders that expressed the transgenic without the production of an obvious change in pigment. Backcrossing of phenotype positive, black and agouti founders to C57 BL/6 mice produced uniform pigmentary changes, described in the Results section.

Histology, Immunohistochemistry, and Electron Microscopy:

Tissues from transgenic and littermate mice were fixed in formalin and embedded in paraffin or polyester wax, sectioned, and stained with hematoxylin and eosin, azure blue, alcian blue, or Giemsa's stain according to standard techniques (31-33). Immunofluorescence studies were performed on polyester wax embedded sections or frozen sections, also using standard techniques. Antibodies included anti-S100 (rabbit anti-cow S100, pre-diluted, Dako, Carpinteria, Calif.), and the ACK2 and ACK4 monoclonal (rat anti-mouse c-kit (34), at 20 µg/ml). Controls included omission of the primary antibody or the use of isotope matched monoclonal antibodies of irrelevant specificity. Electron microscopy was done as previously described (35).

Inflammation Inducement and Treatment

We used Croton Oil and dinitrofluorobenzene (DNFB), respectively to reduce irritant and allergic contact dermatitis, respectively, in HK14-SCF transgenic mice and their nontransgenic liter-mates. Croton Oil was applied directly to the ears of mice and DNFB was applied to the ears of mice after sensitization on shaved abdominal skin. Ear swelling was measured with a micrometer. In the ear-swelling test, the transgenic mice were divided into two groups; one group was treated with the marine monoclonal antibody ACK2, which blocks the interaction of SCF with its receptor (KIT), and the other group was treated with only saline. In addition, shaved abdominal skin of some mice was also treated with Croton Oil or with DNFB, and observed for inflammation and hyperpigmentation.

For statistical analysis, we used a mixed effects model, which allows us to fit repeated measurements over time and to compare different groups over time. We also performed orthogonal contrasts to evaluate the difference between treated and control groups at each time point. Immunoperoxidase study, using anti human SCF monoclonal antibodies, were performed in skin by standard method (7).

Experimental Results

Figure 2A:
Figure 4:
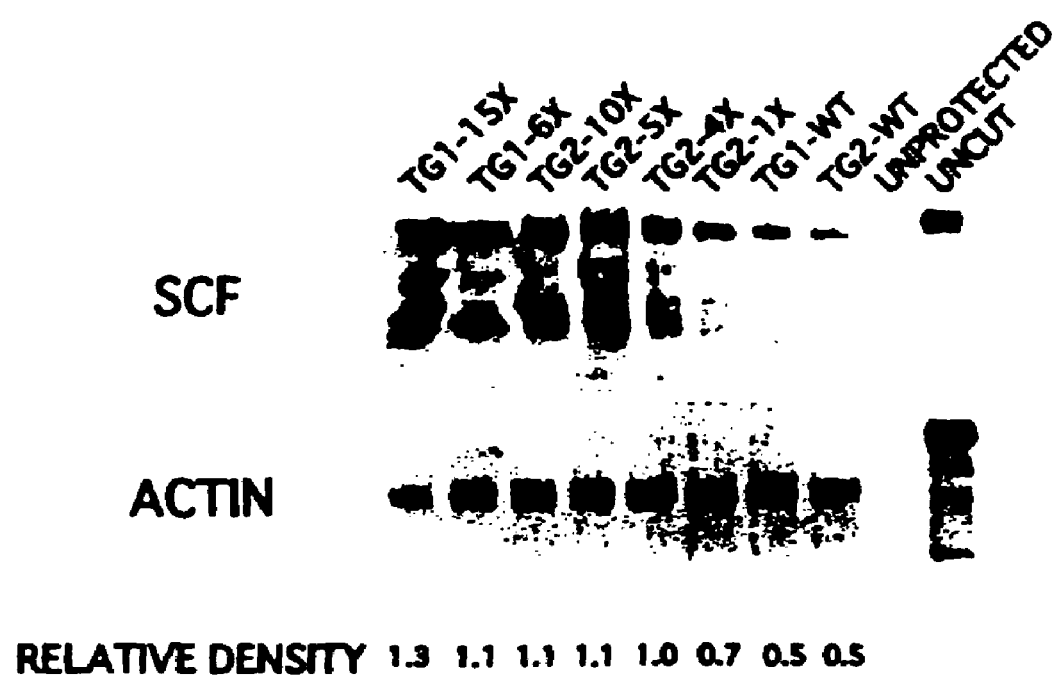

Dermal mast cells accumulate in the presence of membrane/soluble keratinocyte SCF. Sections of skin from all mice producing membrane/soluble SCF (transgenic one) showed increased mast cells in the dermis (FIG. 2). In newborn transgenic one positive mice, the mast cells were superficial near the dermal-epidermal junction, close to the epidermal source of soluble SCF (FIG. 2a). In older mice the mast cells filled the papillary dermis in some areas, but were also present in the reticular dermis, in a pattern identical to that of human mastocytosis (FIG. 2, b-d). Electron microscopic analysis confirmed the presence of numerous mast cells with characteristic granules within the dermis of the transgenic one positive animals, and also showed that some of the heavily pigmented cells within the dermis of transgenic one positive mice were melanocytes (FIG. 3). Mast cells were relatively rare and dermal melanocytes were not detected in the body wall skin of non-transgenic littermates and in transgenic two positive animals of equivalent age. These observations were true across a wide range of copy numbers and levels of SCF mRNA expression (FIG. 4). Since the keratin 14 promoter is properly expressed in the skin only by keratinocytes, and since the production of only membrane-bound keratinocyte SCF did not spontaneously result in increased dermal mast cells in transgenic two positive animals, keratinocyte production of the soluble form of SCF appears to be able to cause cutaneous mastocytosis in mice.

SCF Transgenic Mice are Hyper pigmented:

Targeted expression of each of the SCF transgenic in marine skin caused a similar, distinctive pigmented phenotype. The pigment responsible for the coat color of normal mice resides in the hair follicles and hair shafts, not in the epidermis. The transgenic mice, however, developed prominent epidermal pigmentation (FIG. 5). Transgenic positive animals could be identified by increased pigment at birth. By approximately 21 days of age, the phenotypes were well established; phenotype positive animals showed pigmentation of most of the skin as well as increased pigmentation of most of their skin as well as coat pigment. Extensive pigmentation was noted in a number of areas including the nose, mouth, ears, paws, and external genitalia when compared to normal littermate controls. There was enough individual variation in pigmentation so that no clear correlation between the level of pigmentation and the levels of transgenic expression could be shown. All transgenic animals showed similar degrees of pigmentation regardless of transgenic type, copy number, or levels of SCF mRNA expression. In addition to the epidermal pigmentation, the three transgenic two positive agouti founders showed thin black transverse strips, consistent with the pigment distribution of the allophenic mice described by Beatrice Mintz (pictures not shown) (36).

Figure 2B:
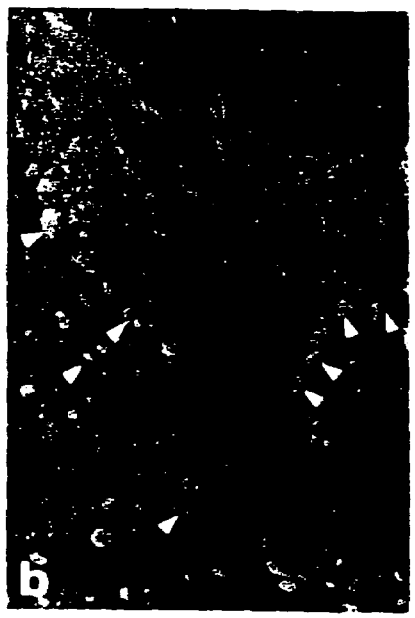
Figure 2C:
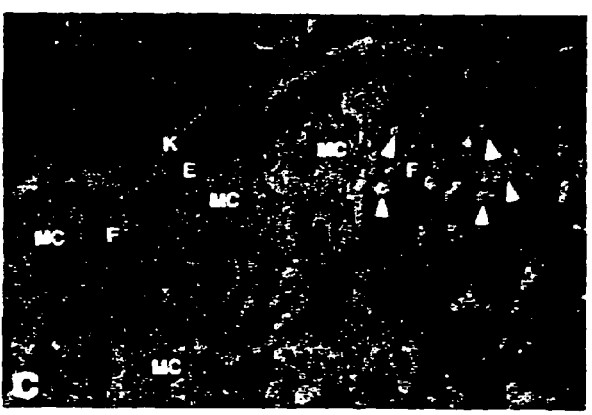
Figure 2D:
Figure 2E:

Numerous Melanocytes are Maintained in the Skin of Transgenic Mice:

The increased pigmentation of the skin of the transgenic positive mice of both types is attributable to the presence of intraepidermal melanocytes, and to the epidermal melanin produced by those cells. Intraepidermal melanocytes can be identified in hematoxylin and eosin stained sections as cells in the basilar layers surrounded by clear halos (FIG. 6, a & b) or in immunoperoxidase preparations by their expression of S-100 protein. Immunohistochemical analysis of animals expressing each of the transgenic showed numerous S-100(+) intraepidermal melanocytes (please also see FIG. 2a). These melanocytes can be differentiated from Langerhans cells, which also express S-100 protein, because melanocytes are in the basal layers and Langerhans are in the suprabasal layers. Melanocytes can also be differentiated from Langerhans cells by their expression of the kit protein, the receptor for SCF, which is not expressed by Langerhans cells. Staining of transgenic animal skin with anti-kit antibody identified well-developed dendrite cells within the basilar layers of the epidermis and follicular epithelium, consistent with melanocytes (FIGS. 6c and 2b).

Histologic examination confirmed the presence of pigment within the epidermis of both transgenic one and transgenic two phenotype positive mice from all sites examined, including the ears, tail, footpads, and body wall (FIG. 6a). In addition, transgenic one positive mice showed many pigmented cells within the dermis. Pigmentary abnormalities were not observed in transgenic negative littermates. Only slight epidermal pigment was identified in these control mice, and mostly in non-hair bearing areas like the footpad and tail. Although pigment patterns were stable throughout much of the adult life of the mice, an occasional TG1 (msSCF) mouse developed patchy areas of regimentation, mostly in the ears, associated with loss of epidermal melanocytes and increased pigment incontinence. This phenomenon was not observed in the mSCF mice.

Figure 7A:
Figure 7B:

Electron microscopy confirmed the presence of numerous melanocytes within the epidermis of both types of transgenic mice (FIG. 7). Pigmented keratinocytes, similar to those seen in the epidermis of humans, were also present in the interadnexal epidermis of the transgenic mice. Intraepidermal melanocytes and pigmented keratinocytes were extremely rare in control mice.

Figure 8:
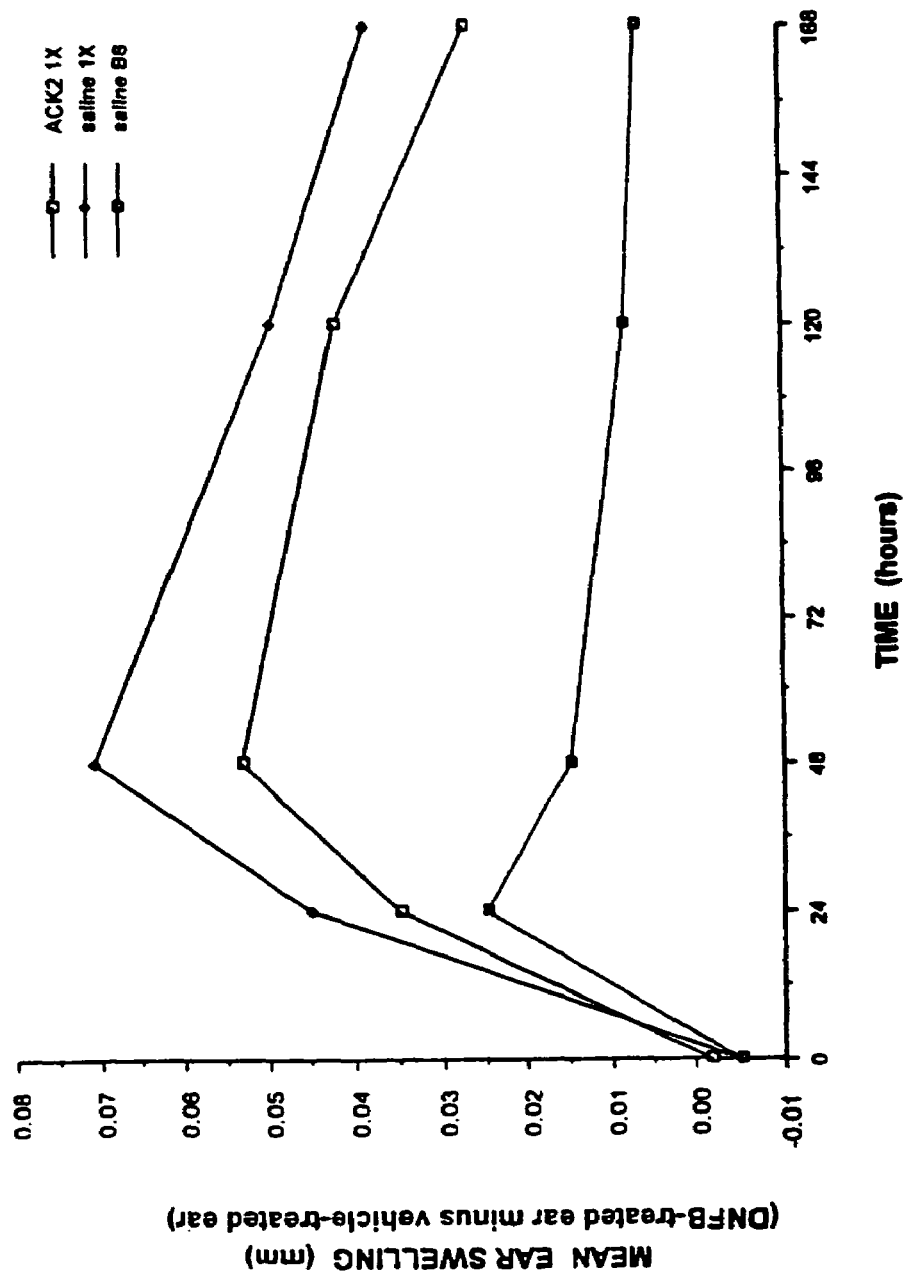
Figure 9A:
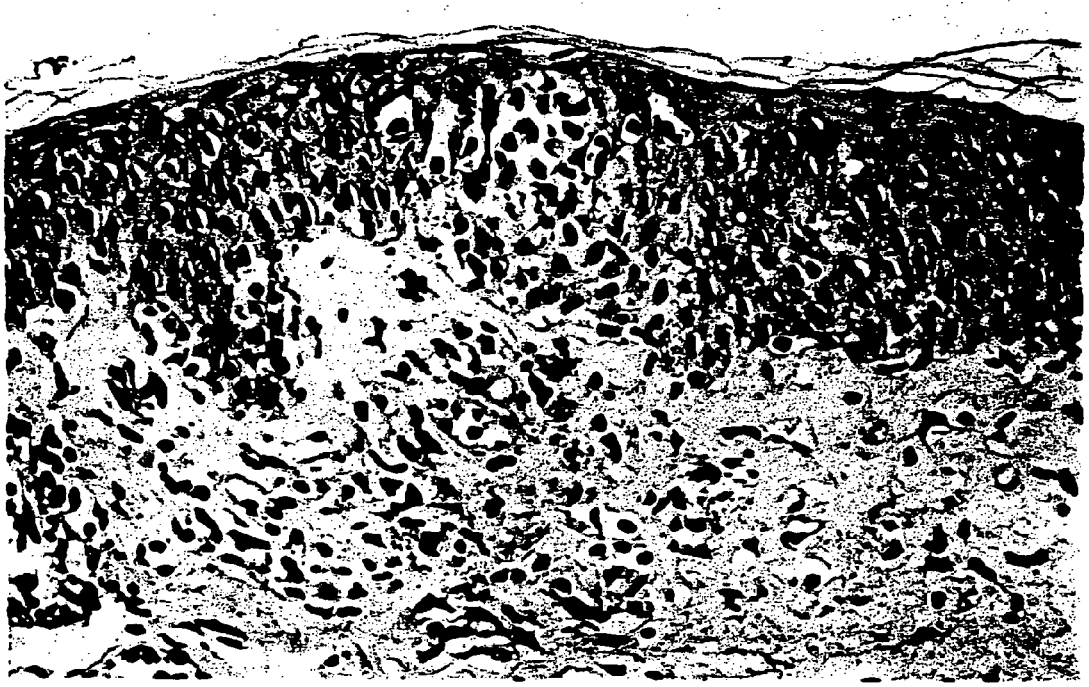
Figure 9B:

All Transgenic Mice Showed Ear Swelling which was Greater in Magnitude and More Prolonged than the Non-Transgenic (B6) Control Mice:

Blocking SCF by administration of ACK2 decreased the magnitude of ear swelling in transgenic mice, as shown in the following FIG. 8.

Averaging Across Time:

There is a difference between the ACK2 treated and the control saline treated transgenic mice, which is significant at the 0.05 level. Averaging across time, there is also a significant difference between each of the two groups of transgenic mice (ACK2 treated and control) and the non-transgenic mice. Both comparisons are statistically significant at the 0.0001 level. See FIG. 8. Observation of the abdominal wall skin treated with Croton Oil or DNFB showed hyperpigmentation and thickening which was not observed in non-transgenic mice control (B6) mice that were treated identically. Histologically, hyperpigmentation correlated with dermal melanophages and increased epidermal melanin, identical to the changes seen in human post inflammatory hyperpigmentation.

Discussion

Melanocytes are maintained in human epidermis throughout life. In normal mice DOPA reaction positive cells (melanoblasts and melanocytes) are found in the epidermis at birth, but their number decreases from postnatal day 4 and is severely reduced after one month of age (37). One possible explanation for the maintenance of epidermal melanocytes in human skin, and the difference between the distribution of melanocytes in adult human and marine skin, could be expression of epidermal SCF. Human epidermal keratinocytes produce SCF (7, 8, 39), but the SCF gene does not appear to be expressed in marine epidermis (9). The results presented here show that SCF expression by marine epidermal keratinocytes causes the maintenance and stimulation of epidermal melanocytes throughout life. These data support the hypothesis that the decrease in melanocyte numbers in the postnatal mouse epidermis is due to a lack of local SCF expression. In combination with the fact that the soluble SCF produced by Sl/Sld mice is insufficient to support normal melanocyte survival and the observations that membrane-bound SCF promotes longer lasting kit activation and increased survival of kit dependent cells in the hematopoietic system (40,41), our data suggest that it is specifically the membrane-bound form of SCF that is crucial for melanocyte survival and function.

It is interesting to note that none of the animals expressing either of the transgenic described in this paper have developed melanoma to date, a finding which supports previous observations that stimulation of the kit tyrosine kinas receptor does not appear to promote the development of melanocytic tumors (40). It also seems likely that the animals described herein, or animals derived from them, will be useful in the study of cutaneous mastocytosis and epidermal melanocyte biology.

The fact that SCF transgenic mice have greater responses to allergic and irritant contactants shows that epidermal SCF can actively contribute to eczematous dermatitis. This interpretation is confirmed by our demonstration that the inflammation can be diminished by blocking the SCF receptor with the ACK2 monoclonal antibody. Since human post natal epidermal keratinocytes express SCF, unlike post natal marine epidermal keratinocytes, and alterations of human epidermal SCF are found in spongiotic dermatitis (a form of eczema), these observations also support our contention that the skin of mice expressing epidermal SCF is a better model of human skin than is the skin of normal mice. Further supporting this claim is our previous observation of increased soluble epidermal SCF in the hyper pigmented lesions of mastocytosis. In sum, these data support our claim that animals expressing epidermal SCF are more suitable for a wide variety of investigations than those which do not.

Additional Experiments

A mouse model of human skin was used in which mice express transgenic SCF driven by the human keratin 1 promoter. Normal mice do not express epidermal SCF postnataly, but humans and the transgenic mice do. The epidermal SCF expressed by humans and by these mice can be solubilized in inflammatory reactions, and based on the data produced, the soluble SCF contributes to the inflammatory process. The trends seen have been repeatedly confirmed in multiple different transgenic lines. The following data are representative of multiple experiments. A series of tests were conducted using croton oil as a skin irritant and 2,4 dinitrofluro-benezne (DNFB) as a contact allergen to induce cutaneous delayed type hypersensitivity (DTH). The results shown in FIGS. 10-11 show that SCF-KIT signaling is directly involved in inflammatory responses and implicate epidermal SCF in both irritant contact dermatitis and cutaneous DTH.

Figure 10:
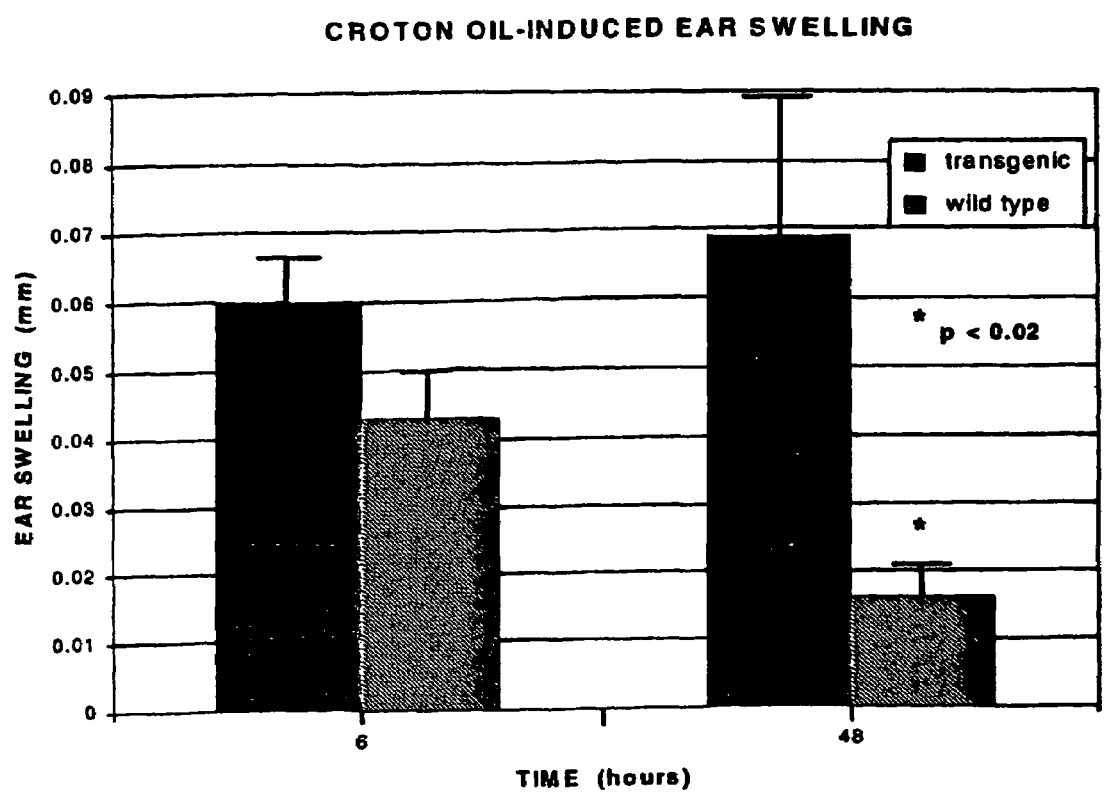
Figure 11:
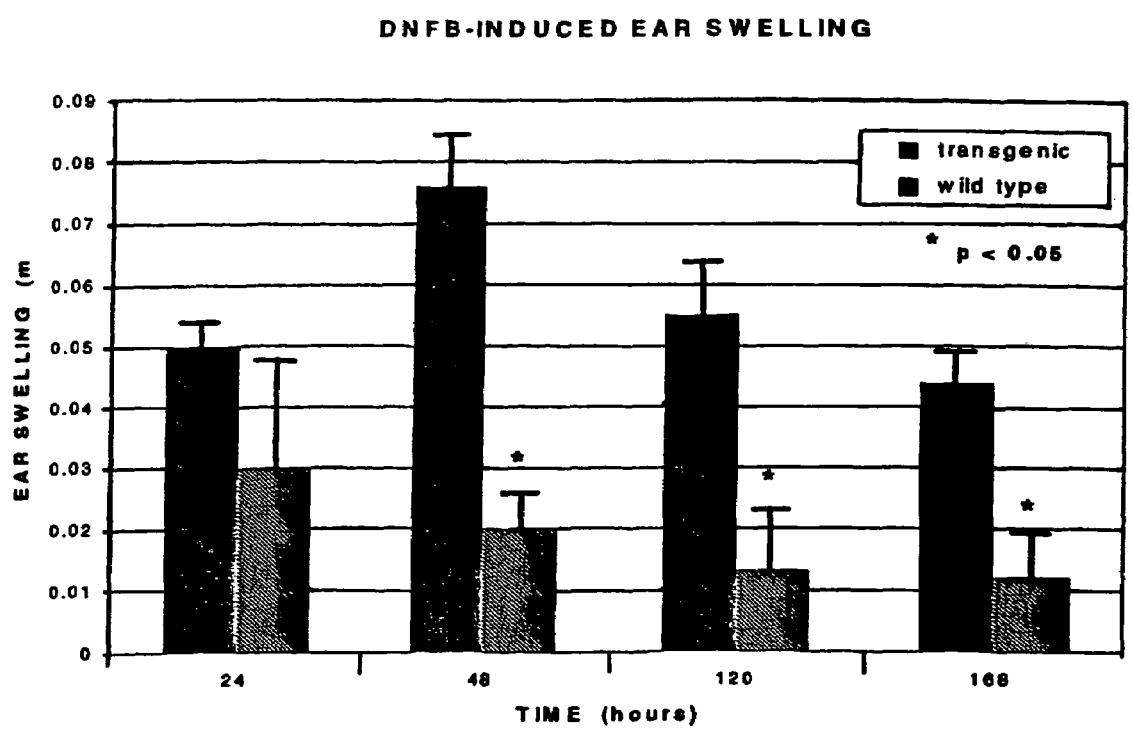
Figure 12:
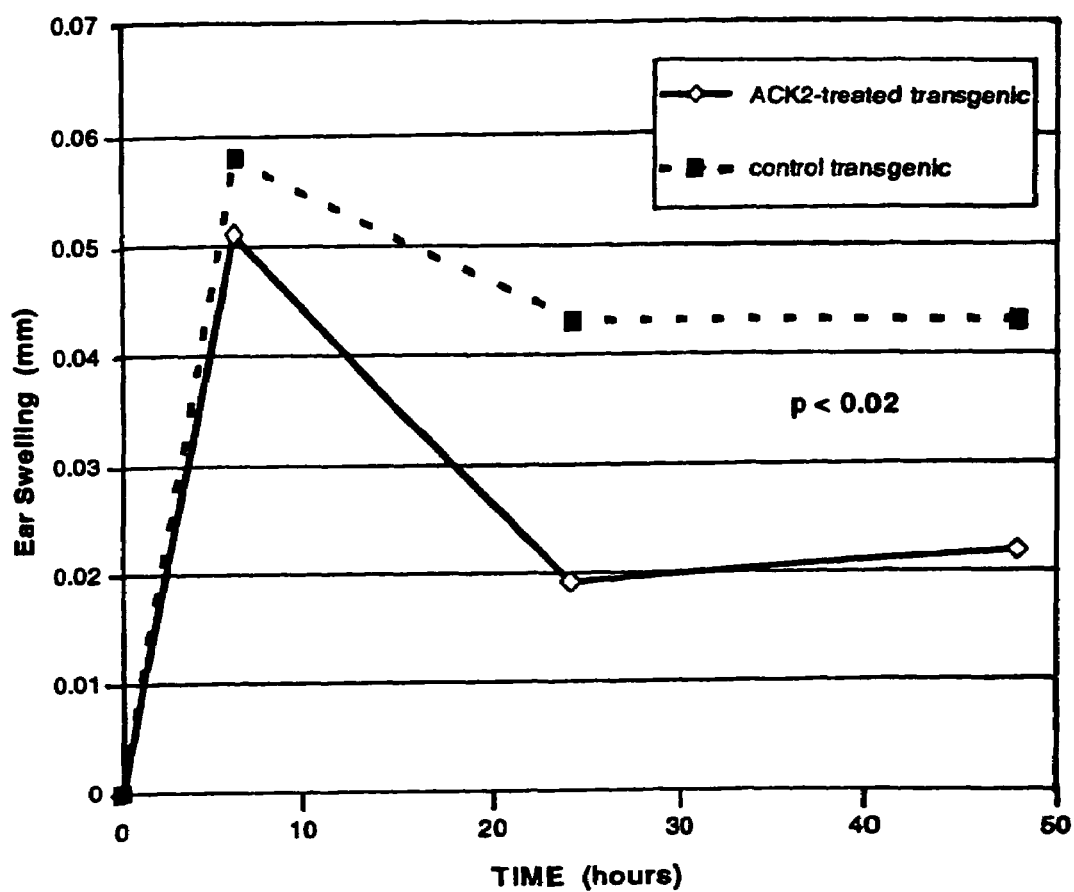

These first experiments demonstrate that irritant dermatitis caused by croton oil is associated with increased ear swelling in epidermal SCF transgenics compared to normal mice (non-transgenic litter mates) (FIG. 10). Similar results were seen with DTH to DNFB (FIG. 11) To further test the hypothesis that SCF-KIT signaling contributes to this inflammation, a monoclonal antibody was used which binds to marine KIT and blocks its activation. As seen in FIGS. 12 and 8, this antibody inhibited the exaggerated ear swelling response seen in the transgenic animals.

It is important to note that the KIT blocking antibody can completely block the additional ear swelling attributable to SCF-KIT signaling in the response to croton oil. This is by definition the efferent (effector) arm of the immune response. The fact that the same antibody treatment does not completely abolish the allergic (DTH) response to DNFB shows, for the first time, that the afferent arm of the immune response is affected by SCF-KIT signaling. Since the antibody completely blocks the efferent effect, as evidenced by complete blocking of the response to croton oil, the portion of the increased transgenic response to DNFB that is not blocked must be attributable to the afferent arm of the immune response. This is a novel concept. Thus, interfering with SCF-KIT signaling during the afferent, sensitization phase of the immune response may be a powerful technique for preventing allergic and other untoward immune responses. For instance, blocking SCF-KIT signaling might be used to induce tolerance or to desensitize individuals to potential environmental sensitizing agents such as workplace chemicals or pollens.

Evidence for the relevance of these observations to human skin may be summarized as follows: a) Normal marine postnatal keratinocytes do not produce SCF; b) it was previously discovered that human epidermal keratinocytes do produce SCF, and that it is normally present predominantly in a cell-associated, membrane-bound form; c) Human epidermal SCF is solubilized in the presence of neoplastic mast cells, presumably by chymase, implying that it may also be solubilized in inflammatory reactions; and d) soluble SCF staining patterns were observed that are similar to, but more subtle than, the volatilization occurring in lesions of cutaneous mastocytosis, in randomly selected cases of human spongiotic dermatitis.

It is believed that past failures to detect a critical role for SCF-KIT signaling in DTH rest on the fact that the mice that have been studied do not express epidermal SCF, and the contribution of SCF to marine cutaneous reactions, if there is any, has therefore been minimal. Since humans do express epidermal SCF, these novel and unexpected results are relevant to human health.

We conclude that inhibition of the SCF-KIT signaling pathway has a beneficial effect in treating human dermatitis of the irritant and DTH types.

REFERENCES

1. Silvers, W. K. (1979) "The coat colors of mice: a model for mammalian gene action and interaction" Springer-Verlag, Inc., New York. pp. 4-5 and references therein;
2. Mayer, T. C. (1970) "A comparison of pigment cell development in albino, steel, and dominant-spotting mutant mouse embryos" *Develop. Biol.*, 23:297-309;
3. Russell, E. S. (1979) "Hereditary anemias of the mouse: a review for geneticists" *Adv. Genet.* 20:357-459;
4. Yarden, Y., et al. (1987) "Human proto-oncogene c-kit: a new cell surface receptor tyrosine kinas for an unidentified ligand" *EMBO J.*, 6:3341-3351;
5. Qiu, F. H., et al. (1988) "Primary structure of c-kit: relationship with the CSF-1/PDGF receptor kinas family—monogenic activation of v-kit involves deletion of extracellular domain and C terminus" *EMBO J.*, 7:1003-1011;
6. Geissler, E. N., et al. (1988) "The dominant-white spotting (W) locus of the mouse encodes the c-kit proto-oncogene" *Cell*, 55:185-192;
7. Longley, B. J. Jr, et al. (1993) "Altered metabolism of mast-cell growth factor (c-kit ligand) in cutaneous mastocytosis" *N. Engl. J. Med.*, 328:1302-1307;
8. Weiss, R. R., et al. (1995) "Human dermal endothelial cells express membrane-associated mast cell growth factor" *J. Invest. Dermatol.*, 104:101-106;
9. Yoshida, H., et al. (1996) "Neural and skin cell specific expression pattern conferred by Steel factor regulatory sequence in transgenic mice" *Developmental Dynamics*, 207:222-232;
10. Anderson, D. M., et al. (1990) "Molecular cloning of mast cell growth factor, a hematopoietic that is active in both membrane bound and soluble forms" *Cell*, 63:235-243;
11. Zsebo, K. M., et al. (1990) "Identification, purification, and biological characterization of hematopoietic stem cell factor from Buffalo rat liver-conditioned medium" *Cell*, 63:195-201;
12. Flanagan, J. G. and P. Leder (1990) "The kit ligand: a cell surface molecule altered in steel mutant fibroblasts" *Cell*, 63:185-194;
13. Onoue, H., et al. (1989) "Suppressive effects of Sl/Sld mouse embryo-derived fibroblast cell lines on diffusible factor-dependent proliferation of mast cells" *Blood*, 74:1557-1562;
14. Anderson, D. M., et al. (1991) "Alternate splicing of mRNAs encoding human mast cell growth factor and localization of the gene to chromosome 12q22-q24" *Cell Growth & Development*, 2:373-378;
15. Lu, H. S., et al. (1991) "Amino acid sequence and post-translational modification of stem cell factor isolated from buffalo rat liver cell-conditioned medium" *J. Biol. Chem.*, 266:8102-8107;
16. Flanagan, J. G., et al. (1991) "Transmembrane form of the kit ligand growth factor is determined by alternative splicing and is missing Sld mutant" *Cell*, 64:1025-1035;
17. Brannan, C. I., et al. (1991) "Steel-Dickie mutation encodes a c-Kit ligand lacking transmembrane and cytoplasmic domains" *Proc. Natl. Acad. Sci. USA*, 88:4671-4674;
18. Zsebo, K. M., et al. (1990) "Stem cell factor is encoded at the Sl locus of the mouse and is the ligand for the c-kit tyrosine kinase receptor" *Cell*, 63:213-224;
19. Huang, E. J., et al. (1992) "Differential expression and processing of two cell associated forms of the kit-ligand: KL-1 and KL-2" *Mol. Biol. Cell*, 3:349-362;
20. Wehrle-Haller, B. and J. A. Weston (1995) "Soluble and cell-bound forms of steel factor activity play distinct roles in melanocyte precursor dispersal and survival on the lateral neural crest migration pathway" *Development*, 121:731-742;
21. Tsai, M., et al. (1991) "The rat c-kit ligand, stem cell factor, induces the development of connective tissue-type and mucosal mast cells in vivo: Analysis by anatomical distribution, photochemistry, and protease phenotype" *J. Exp. Med.*, 174:125-131;
22. Harrist, T. J., et al. (1995) "Recombinant human stem cell factor (SCF) (c-kit ligand) promotes melanocyte hyperplasia and activation in vivo" *Lab. Invest.*, 72:48A;
23. Costa, J. J., et al. (1996) "Recombinant human stem cell factor (KIT ligand) promotes human mast cell and melanocyte hyperplasia and functional activation in vivo" *J. Exp. Med.*, 183:2681-2686;
24. Longley, B. J., et al. (1995) "The mast cell and mast cell disease" *J. Am. Acad. Dermatol.*, 32:545-561;
25. Longley, B. J., et al. (1996) "Somatic c-KIT activating mutation in urinary pimentos and aggressive mastocytosis: establishment of clonality in a human mast cell neoplasm" *Nature Genetics*, 12:312-314;
26. Furitsu, T., et al. (1993) "Identification of mutations in the coding sequence of the proto-oncogene c-KIT in a human mast cell leukemia cell line causing ligand-independent activation of c-KIT product" *J. Clin. Invest.*, 92:1736-1744;
27. Vassar, R., et al. (1989) "Tissue-specific and differentiation-specific expression of a human K14 keratin gene in transgenic mice" *Proc. Natl. Acad. Sci. USA*, 86:1563-1567;
28. Williams, D. E., et al. (1990) "Identification of a ligand for the c-kit proto-oncogene" *Cell*, 1990; 63:167-174;
29. Majumdar, M. K., et al. (1994) "Identification and mutation of primary and secondary proteolytic cleavage sites in murine stem cell factor cDNA yields biologically active, cell-associated protein" *J. Biol. Chem.*, 269:1237-1242;
30. Yasunaga, M., et al. (1995) "Cell cycle control of c-kit-1 IL-7R1B precursor cells by two distinct signals derived from IL-7 receptor and c-kit in a fully defined medium" *J. Exp. Med.*, 182:315-323;
31. Kunisada, T., et al. (1996) "Characterization and isolation of melanocyte progenitors from mouse embryos" *Development Growth & Differentiation*, 38:87-97;
32. Yoshida, H., et al. (1996) "Distinct stages of melanocyte differentiation revealed by analysis of nonuniform pigmentation patterns" Development, 122:1207-1214;
33. Scott, J. E. and R. T. Mowry (1970) "Alcian blue—a consumer's guide" *J. Histochem Cytochem.*, 18:842;

34. Nishikawa, S., et al. (1991) "In utero manipulation of coat color formation by a monoclonal anti-c-kit antibody: two distinct waves of c-kit-dependency during melanocyte development" *EMBO J.*, 10:2111-2118;
35. Okura, M., et al. (1995) "Effects of monoclonal anti-c-kit antibody (ACK2) on melanocytes in newborn mice" *J. Invest. Dermatol.*, 105:322-328;
36. Bradl, M., et al. (1991) "Clonal coat color variation due to a transforming gene expressed in melanocytes of transgenic mice" *Proc. Natl. Acad. Sci. USA*, 88:6447-6451;
37. Grichnik, J. M., et al. (1995) "Human recombinant stem-cell factor induces melanocytic hyperplasia in susceptible patients" *J. Am. Acad. Dermatol.*, 33:577-583;
38. Hirobe, T. (1984) "Histochemical survey of the distribution of the epidermal melanoblasts and melanocytes in the mouse during fetal and postnatal periods" *Anat. Rec.*, 208:589-594;
39. Hamann, K., et al. (1995) "Expression of stem cell factor in cutaneous mastocytosis" *Br. J. Dermatol.*, 133:203-208;
40. Funasaka, Y., et al. (1992) "C-kit-kinase induces a cascade of protein tyrosine phosphorylation in normal human melanocytes in response to mast cell growth factor and stimulates mitogen-activated protein kinase but is down-regulated in melanomas" Mol. Biol. Cell, 3:197-209.

Second Series

Mastocytosis is a neoplastic disease caused at least in part by somatic mutations of the c-KIT proto-oncogene resulting in constitutive activation of its protein product, KIT, the receptor tyrosine kinase for stem cell factor. KIT stimulates mast cell proliferation and prevents apoptosis of neoplastic mast cells. Human gastrointestinal stromal tumor cells also express mutated and activated kit (Hirota et al 1998). To develop potential therapies for mastocytosis and gastrointestinal stromal tumor cells we used indolinones, small molecules which inhibit tyrosine kinases.

The proto-oncogene c-KIT encodes KIT (Yarden et al, 1987; Qiu et al, 1988), the receptor tyrosine kinase for stem cell factor (Martin et al, 1990), also known as mast cell growth factor. Somatic c-KIT mutations causing ligand-independent activation of KIT and cell transformation (Furitsu et al, 1993; Kitayama et al, 1995; Tsujimura et al, 1996; Hirota et al, 1998; Ma et al, 1999a) appear causal in certain types of mastocytosis (Nagata et al, 1995; Longley et al, 1996, 1999; Ma et al, 1999a).

Documented activating c-KIT mutations fall into two groups. One group consists of mutations in codon 816 of human c-KIT, or its equivalent positions in other species, resulting in single residue substitution for Asp816 in the activation loop of the receptor kinase domain (Ma et al, 1999a). The other group of activating mutations includes single residue substitutions and in-frame insertions or deletions in the receptor intracellular juxtamembrane region, which disrupt intramolecular inhibition of the kinase by a putative juxtamembrane α-helix (Ma et al, 1999b). All sporadic adult-onset mastocytosis patients examined to date, and a subset of pediatric cases with atypical clinical presentations, have activating codon 816 mutations (Longley et al, 1999), whereas activating juxtamembrane mutations are common in canine mastocytomas (Ma et al, 1999a) and in human gastrointestinal stromal tumors (Hirota et al, 1998).

REFERENCES FOR SECOND SERIES

Furitsu T, Tsujimura T, Tono T, Ikeda H, Kitayama H, et al: Identification of mutations in the coding sequence of the proto-oncogene c-kit in a human mast cell leukemia cell line causing ligand-independent activation of c-kit product. *J Clin Invest* 92: 1736-1744, 1993

Hirota S, Isozaki K, Moriyama Y, Hashimoto K, Nishida T, et al: Gain-of-function mutations of c-kit in human gastrointestinal stromal tumors. *Science* 279: 577-580, 1998

Kitayama H, Kanakura Y, Furitsu T, Tsujimura T, Oritani K, et al: Constitutively activating mutations of c-kit receptor tyrosine kinase confer factor-independent growth and tumorigenicity of factor-dependent hematopoietic cell lines. *Blood* 85: 790-798, 1995

Longley B J, Tyrrell L, Lu S, Ma Y, Langley K, et al: Somatic c-KIT activating mutation in urticaria pigmentosa and aggressive mastocytosis: establishment of clonality in a human mast cell neoplasm. *Nature Genet* 12: 312-314, 1996

Longley B J, Metcalfe D D, Tharp M, Wang X, Tyrrell L, et al: Activating and dominant inactivating c-KIT catalytic domain mutations in distinct clinical forms of human mastocytosis. *Proc Natl Acad Sci USA* 96: 1609-1614, 1999

Ma Y, Longley B J, Wang X, Blount J L, Langley K, Caughey G H: Clustering of activating mutations in c-KIT's juxtamembrane coding region in canine mast cell neoplasms. *J Invest Dermatol* 112: 165-170, 1999a Ma Y, Cunningham M E, Wang X, Ghosh I, Regan L, Longley B J: Inhibition of spontaneous receptor phosphorylation by residues in a putative α-helix in the KIT intracellular juxtamembrane region. *J Biol Chem* 274: 13399-13402, 1999b Martin F H, Suggs S V, Langley K E, Lu H S, Ting J, et al: Primary structure and functional expression of rat and human stem cell factor DNAs. *Cell* 63: 203-211, 1990

Nagata H, Worobec A S, Oh C K, Chowdhury B A, Tannenbaum S, et al: Identification of a point mutation in the catalytic domain of the protooncogene c-kit in peripheral blood mononuclear cells of patients who have mastocytosis with an associated hematologic disorder. *Proc Natl Acad Sci USA* 92: 10560-10564, 1995

Tsujimura T, Morimoto M, Hashimoto K, Moriyama Y, Kitayama H, et al: Constitutive activation of c-kit in FMA3 murine mastocytoma cells caused by deletion of seven amino acids at the juxtamembrane domain. *Blood* 87: 273-283, 1996

Yarden Y, Kuang W-J, Yang-Feng T, Coussens L, Munemitsu S, et al: Human proto-oncogene c-kit: a new cell surface receptor tyrosine kinase for an unidentified ligand. *EMBO J* 6: 3341-3351, 1987

Third Series of Experiments

Passive Anaphylaxis: SCF and KIT stimulation have a number of effects on mast cells in vitro, but it is not clear what the overall of effects of blocking KIT would be on inflammation and physiology in vivo. For instance, numerous studies have shown that recombinant SCF causes mast cell activation, directly stimulates mediator release, and alters the threshold for IgE dependent mediator release in vitro (Nakajima et al. Biochem. Biophys. Res. Commun. 1992) (Coleman et al. J. Immunol. 1993) (Columbo et al. 1992) (Bischoff et al. J. Exp. Med. 1992). Furthermore, a single injection of recombinant SCF causes mast cell activation in mice (Werschil et al. J. Exp. Med. 1992). However, daily administration of recombinant SCF to mice results in mast cell hyperplasia which varies at different anatomic sites, but does not result in mast cell activation (Anado et al. J. Clin. Invest. 1993), and the chronic administration of recombinant SCF to mice has variable effects on passive anaphylaxis reactions. Chronic stimulation with recombinant SCF followed by elicitation of passive anaphylaxis results in increased mast cell activation at some anatomic sites but not others and, surprisingly, a decrease in deaths in mice (Anado et al. J. Clin. Invest. 1993). This last result is counter-intuitive and indicates that exact effects of blocking KIT activation in vivo cannot be predicted accurately based on in vitro data. The authors themselves describe the results as unexpected.

To investigate the effects of blocking KIT in vivo, the ACK2 KIT-blocking-antibody and passive cutaneous anaphylaxis were used in the following experiments:

The skin of Balb/c mice was sensitized by an intradermal injection of murine monoclonal IgE specific for dinitrophenyl hapten. A second set of mice was sensitized with both the IgE and ACK2. 24 hours later, dinitrophenylated human serum albumin was injected into the tail veins of the mice in a mixture of 1% Evans' Blue dye (1 mg). Mice were observed for anaphylaxis, and thirty minutes later were sacrificed. The dorsal skin at the area of sensitization was removed for measurement of the amount of extravasated dye. The amount of dye was determined colorometrically after extraction of the skin in 1 ml of 1 Normal KOH overnight, at 37 degrees centigrade. 0.6 Normal phosphoric acid in acetone (15:13) was added and the mixture cleared by centrifugation. The absorbent intensity (OD) of the supernatant was measured at 620 nm spectrophotometrically. The amount of extravasated dye, which is a measure of anaphylaxis, was significantly reduced in the presence of ACK2 (mean OD 0.0223) when compared to animals sensitized without ACK2 (OD 0.0617) a difference which was significant with p<0.01, and the animals treated with ACK2 showed less respiratory distress compared to animals without ACK2.

These data demonstrate, for the first time, that blocking the SCF-KIT signaling pathway in vivo can decrease anaphylaxis and bronchospasms. Combined with the data on cutaneous inflammation, they demonstrate that the SCF-KIT pathway is actively involved in inflammatory reactions in vivo, rather than playing merely a supportive role in the development and maintenance of KIT expressing cells. This critical finding shows that acute blockage of the SCF-KIT signaling pathway can inhibit inflammation.

Additional Experiments

Figure 13:
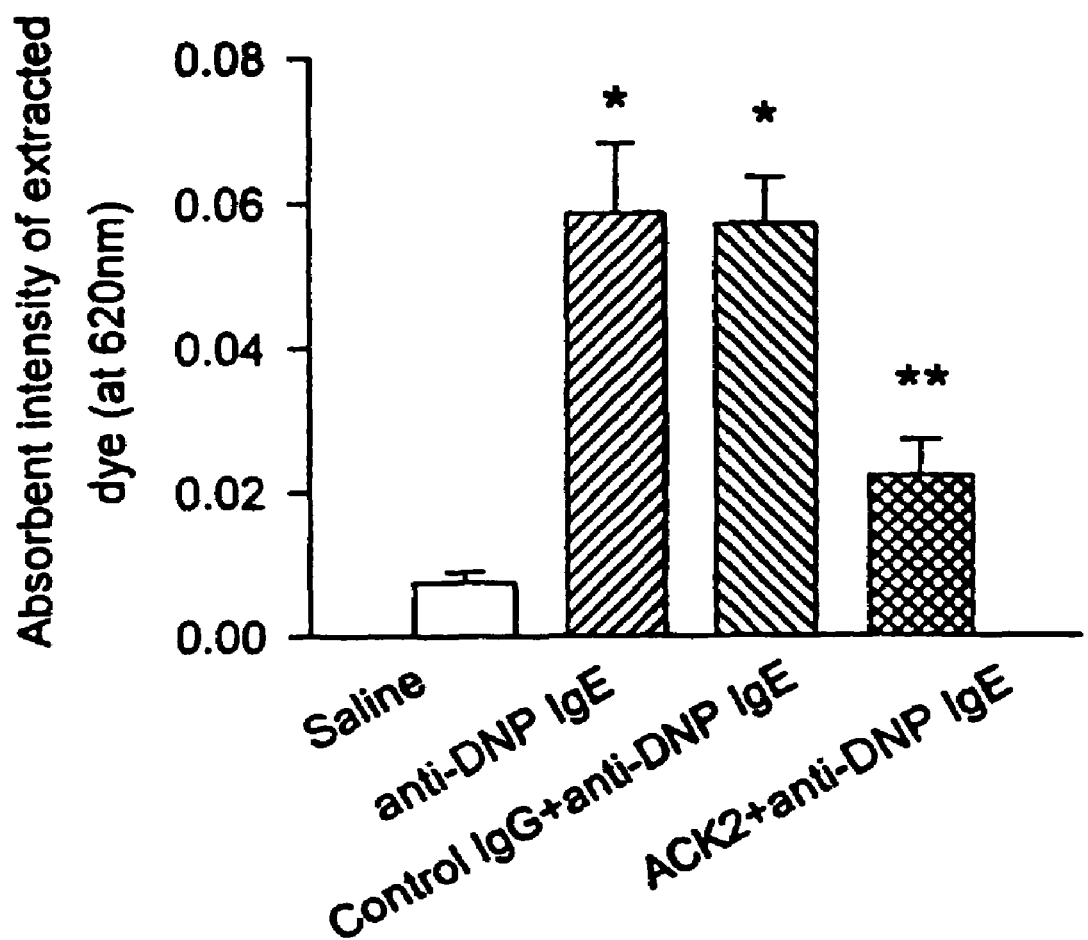

A KIT blocking antibody was used to determine that SCF-KIT signaling plays an important role in vivo in passive cutaneous anaphylaxis. This suggests that SCF potentiation of IgE receptor signaling is important in vivo. (FIG. 13). These are the first in vivo data to suggest that blocking the SCF-KIT signaling pathway would be useful therapeutically for conditions like asthma and allergic rhinitis.

REFERENCES FOR THIRD SERIES OF EXPERIMENTS

1. Nakajima K, Hirai K, Yamaguchi M, Takaishi T, Ohta K, Morita Y, Ito K. Biochem. Biophys. Res. Commun. 1992, 183:1076-83.
2. Coleman J W, Holliday M R, Kimber I, Zsebo K M and Galli S J. J. Immunol. 1993, 150: 556-62.
3. Columbo M, Horowitz E M, Botana L M, MacGlashan D W Jr., Bochner B S, Gillis S, Zsebo K M, Galli S J, Lichtenstein L M. J. Immunol. 1992, 149:599-608.
4. Bischoff S C and Dahinden C A. J. Exp. Med. 1992, 175:237-44.
5. Wershil B K, Tsai M, Geissler E N, Zsebo K M, Galli S J. J. Exp. Med. 1992, 175:245-55.
6. Ando A, Martin T R, Galli S J. J. Clin. Invest. 1993, 92:1639-49.

What is claimed:

1. A method of desensitizing a subject to an agent which comprises administering to the subject an amount of an antibody or portion thereof that binds to kit protein in an amount effective to inhibit the kinase enzymatic reaction of kit protein and to inhibit the stem cell factor signaling pathway, thereby desensitizing the subject to the agent.

* * * * *